US012605208B2

(12) United States Patent
Plessers et al.

(10) Patent No.: US 12,605,208 B2
(45) Date of Patent: Apr. 21, 2026

(54) SURGERY PLANNING SYSTEM WITH AUTOMATED DEFECT QUANTIFICATION

(71) Applicant: Materialise N.V., Leuven (BE)

(72) Inventors: Katrien Plessers, Leuven (BE); Filip Jonkergouw, Leuven (BE); Maarten Zandbergen, Leuven (BE); Nele Daemen, Leuven (BE); Janelle Schrot, Leuven (BE)

(73) Assignee: Materialise N.V., Leuven (BE)

( * ) Notice: Subject to any disclaimer, the term of this patent is extended or adjusted under 35 U.S.C. 154(b) by 1177 days.

(21) Appl. No.: 17/453,728

(22) Filed: Nov. 5, 2021

(65) Prior Publication Data

US 2022/0054197 A1 Feb. 24, 2022

Related U.S. Application Data

(63) Continuation of application No. PCT/US2020/032165, filed on May 8, 2020.

(60) Provisional application No. 62/845,676, filed on May 9, 2019.

(51) Int. Cl.
| | |
|---|---|
| *A61B 34/10* | (2016.01) |
| *G16H 30/40* | (2018.01) |
| *G16H 50/20* | (2018.01) |
| *G16H 50/50* | (2018.01) |

(52) U.S. Cl.
CPC ............. *A61B 34/10* (2016.02); *G16H 30/40* (2018.01); *G16H 50/20* (2018.01); *G16H 50/50* (2018.01); *A61B 2034/105* (2016.02)

(58) Field of Classification Search
None
See application file for complete search history.

(56) References Cited

U.S. PATENT DOCUMENTS

| | | |
|---|---|---|
| 2008/0235052 A1 | 9/2008 | Node-Langlois et al. |
| 2014/0278322 A1 | 9/2014 | Jaramaz et al. |
| 2016/0331463 A1 | 11/2016 | Nötzli et al. |
| 2019/0090952 A1 | 3/2019 | Bonny et al. |

FOREIGN PATENT DOCUMENTS

| | | |
|---|---|---|
| CN | 104519808 A | 4/2015 |
| CN | 105228548 A | 1/2016 |
| WO | 2013165867 A2 | 11/2013 |

OTHER PUBLICATIONS

Swennen GRJ. Three-dimensional treatment planning of orthognathic surgery in the era of virtual imaging. Journal of Oral and Maxillofacial Surgery 67(10): 2080-2092. (Year: 2009).*
Sintini I. Statistical shape and intensity modeling of the shoulder. University of Denver dissertation, 1478, 99 pgs. (Year: 2017).*
Kocsis G. A new classification of glenoid bone loss to help plan the implantation of a glenoid component before revision arthroplasty of the shoulder. The Bone & Joint Journal 98: 374-380. (Year: 2016).*
Hacihaliloglu I. 3D ultrasound for orthopedic interventions. Advances in Experimental Medicine and Biology 1093, Chapter 10, pp. 113-129. (Year: 2018).*
Heimann, Tobias et al., Statistical Shape Models for 3D Medical Image Segmentation: A Review, Medical Image Analysis, Oxford University Press, Aug. 1, 2009, pp. 543-563, 13:4, Oxford, GB.
Plessers, Katrien et al., Automated Quantification of Glenoid Bone Defects Using 3-Dimensional Measurements, Journal of Shoulder and Elbow Surgery, Jan. 23, 2020, pp. 1050-1058, 29:5, Mosby, Amsterdam, NL.
International Search Report dated Jul. 8, 2020 for International Patent Application No. PCT/US2020/032165.

* cited by examiner

*Primary Examiner* — Olivia M. Wise
*Assistant Examiner* — Robert J. Kallal
(74) *Attorney, Agent, or Firm* — Dinsmore & Shohl LLP

(57) ABSTRACT

Certain aspects of the present disclosure provide techniques for preparing medical treatment plans, comprising: acquiring medical image data associated with an anatomy of a patient; creating a three-dimensional anatomy model based on the medical image data; fitting a statistical shape model to the three-dimensional anatomy model; determining one or more quantitative measurements based on the fitted statistical shape model; and classifying a defect associated with the anatomy of the patient based on the one or more quantitative measurements.

20 Claims, 29 Drawing Sheets

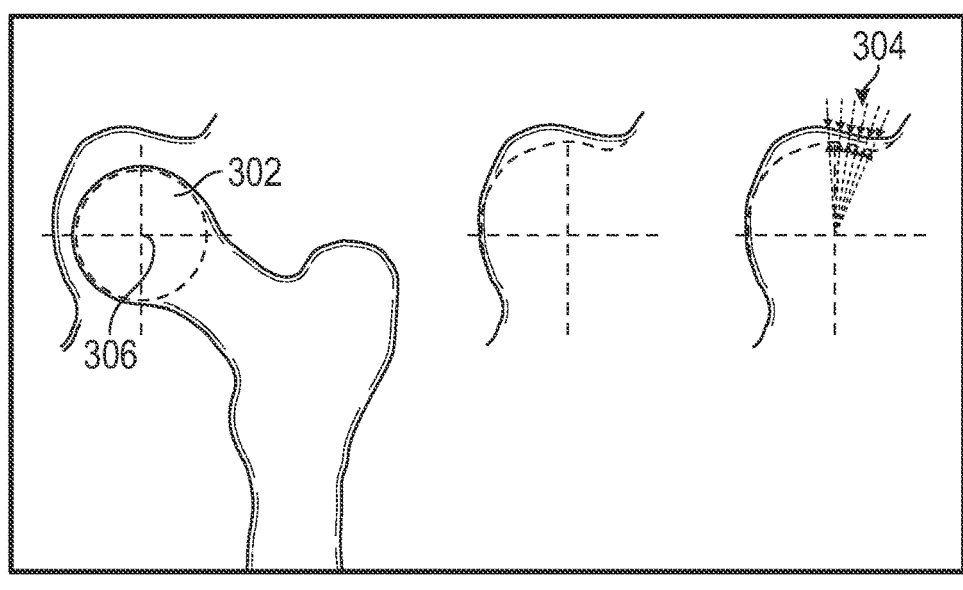
FIG. 3
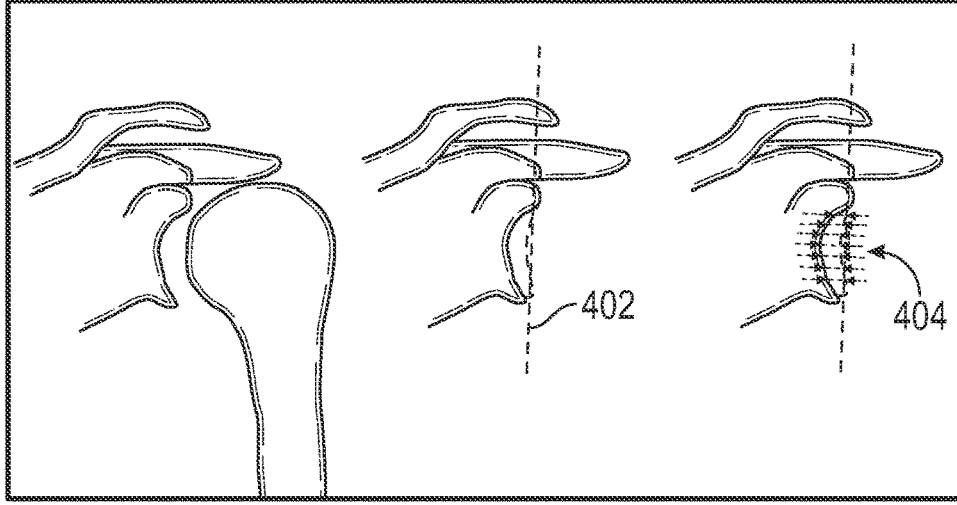
FIG. 4
$$d_i^{max}$$
504
$$d_i^{vault}$$
502
$$d_i^{ero}$$
506
506
FIG. 5

Deltoid Elongation = 21mm
Subscapularis Elongation= -26mm
Infraspinatus Elongation = 21mm
Deltoid Moment Arm = 21mm

2002

2002

2202

Anatomic femoral valgus angle: 4.0°

2602

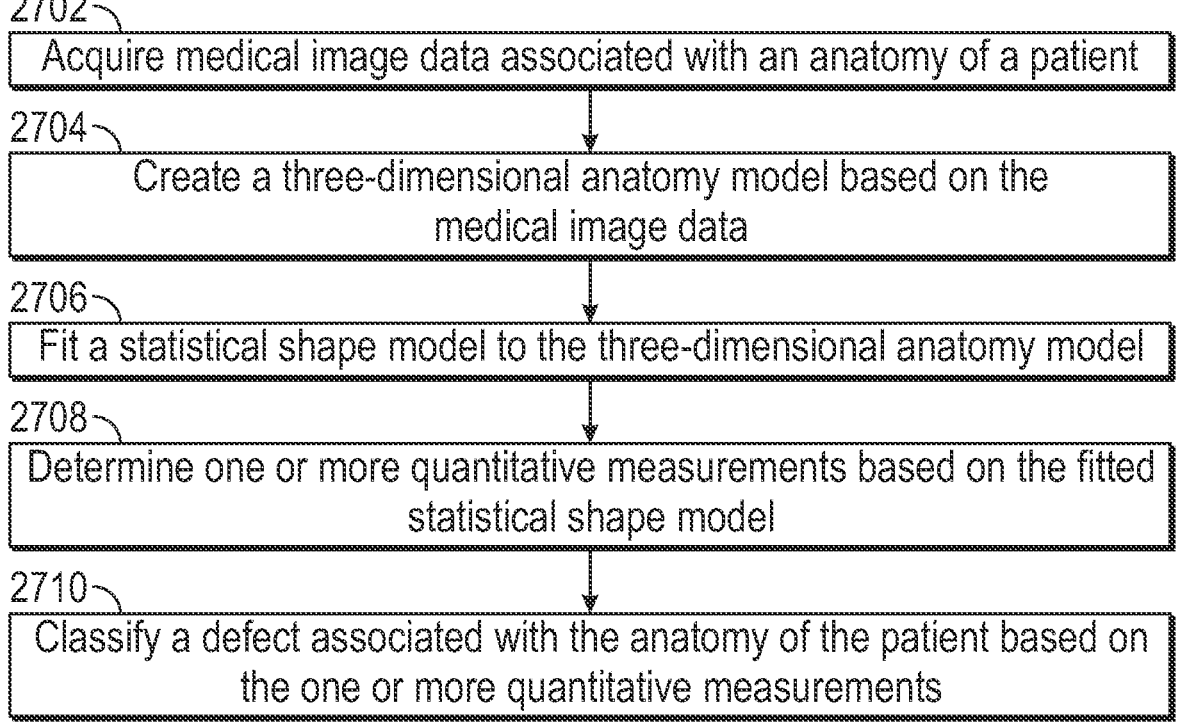

2702 —
Acquire medical image data associated with an anatomy of a patient

2704 —
Create a three-dimensional anatomy model based on the
medical image data

2706 —
Fit a statistical shape model to the three-dimensional anatomy model

2708 —
Determine one or more quantitative measurements based on the fitted
statistical shape model 2710 —
Classify a defect associated with the anatomy of the patient based on
the one or more quantitative measurements

FIG. 27

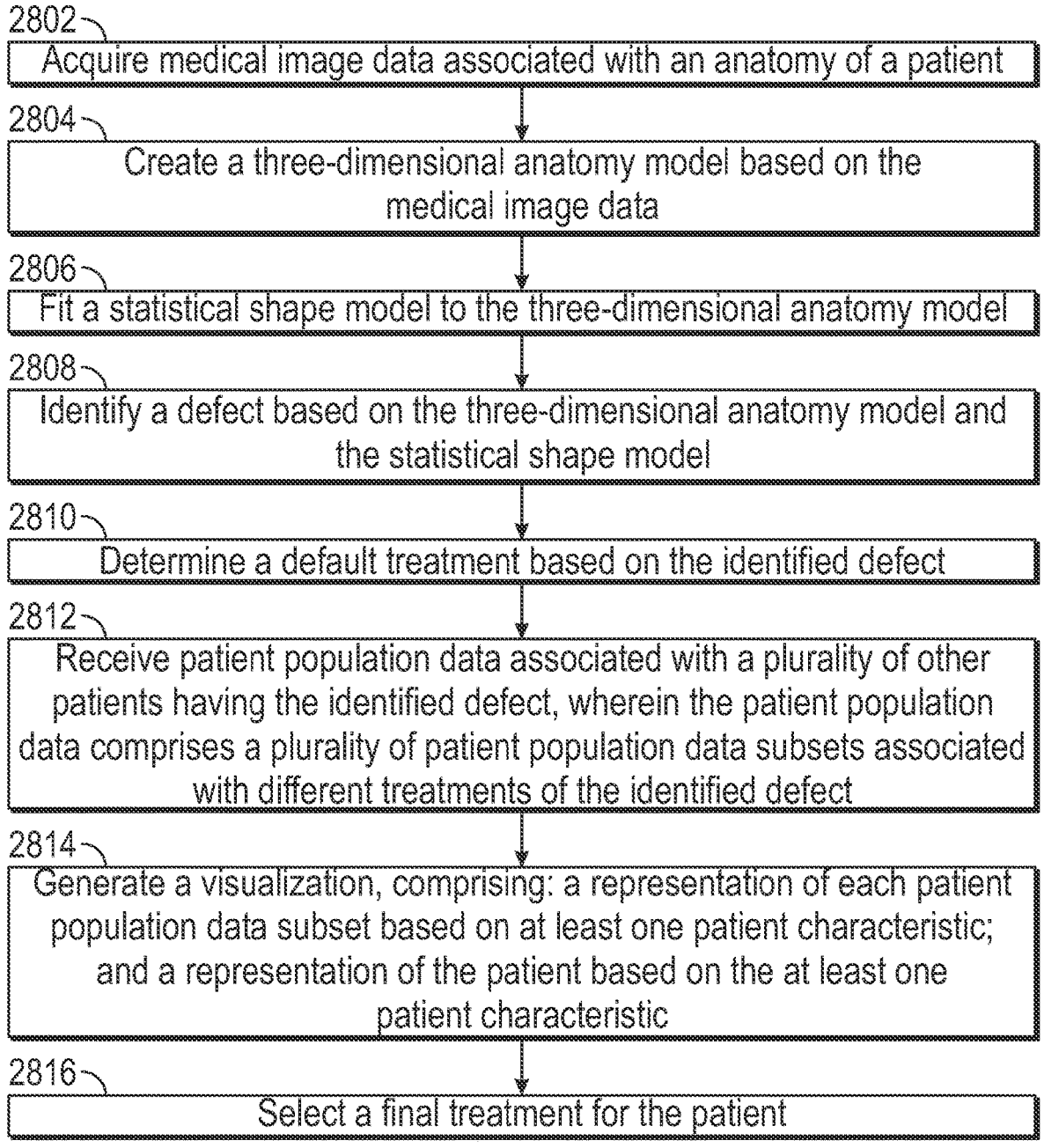

2802
Acquire medical image data associated with an anatomy of a patient

2804
Create a three-dimensional anatomy model based on the
medical image data

2806
Fit a statistical shape model to the three-dimensional anatomy model

2808
Identify a defect based on the three-dimensional anatomy model and
the statistical shape model 2810
Determine a default treatment based on the identified defect 2812
Receive patient population data associated with a plurality of other
patients having the identified defect, wherein the patient population
data comprises a plurality of patient population data subsets associated
with different treatments of the identified defect 2814
Generate a visualization, comprising: a representation of each patient
population data subset based on at least one patient characteristic;
and a representation of the patient based on the at least one
patient characteristic 2816
Select a final treatment for the patient

FIG. 28

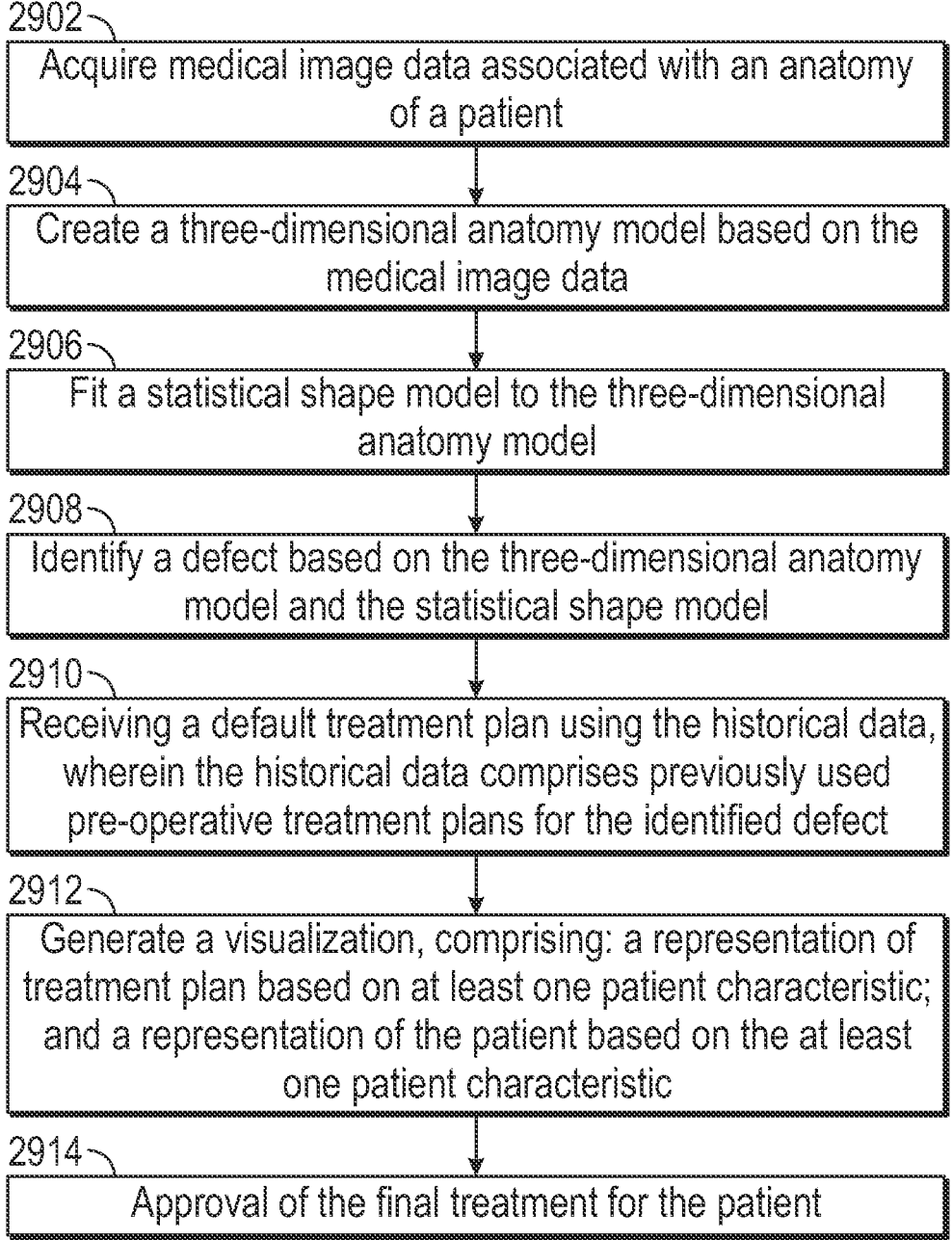

2902 — Acquire medical image data associated with an anatomy of a patient

2904 — Create a three-dimensional anatomy model based on the medical image data

2906 — Fit a statistical shape model to the three-dimensional anatomy model

2908 — Identify a defect based on the three-dimensional anatomy model and the statistical shape model 2910 — Receiving a default treatment plan using the historical data, wherein the historical data comprises previously used pre-operative treatment plans for the identified defect 2912 — Generate a visualization, comprising: a representation of treatment plan based on at least one patient characteristic; and a representation of the patient based on the at least one patient characteristic 2914 — Approval of the final treatment for the patient

FIG. 29

SURGERY PLANNING SYSTEM WITH AUTOMATED DEFECT QUANTIFICATION

CROSS-REFERENCE TO RELATED APPLICATIONS

This application is a continuation of International Application No. PCT/US2020/032165, filed May 8, 2020, which claims the benefit of and priority to U.S. Provisional Patent Application No. 62/845,676, filed on May 9, 2019, the entire contents of each of which are incorporated herein by reference.

INTRODUCTION

Aspects of the present disclosure relate to surgery planning systems, including surgery planning systems with automated defect quantification and population-based decision support capabilities.

Conventional surgery planning tools deal with pre-operative planning procedures. They address the conventional issues associated with a specific surgery such as sizes and design of various components including surgical instruments and implants, location and orientation of implants and fixation devices. They typically take medical images of the patient as input, and therefore allow the user—medical professional or non-medical professional, such as technician or engineer—to make decisions based only on the information available in those images.

BRIEF SUMMARY

Certain aspects provide a method for preparing medical treatment plans, comprising: acquiring medical image data associated with an anatomy of a patient; creating a three-dimensional anatomy model based on the medical image data; fitting a statistical shape model to the three-dimensional anatomy model; determining one or more quantitative measurements based on the fitted statistical shape model; and classifying a defect associated with the anatomy of the patient based on the one or more quantitative measurements.

Further aspects provide a method for determining a treatment for an anatomical defect, including: acquiring medical image data associated with an anatomy of a patient; creating a three-dimensional anatomy model based on the medical image data; fitting a statistical shape model to the three-dimensional anatomy model; identifying a defect based on the three-dimensional anatomy model and the statistical shape model; determining a default treatment based on the identified defect; receiving patient population data associated with a plurality of other patients having the identified defect, wherein the patient population data comprises a plurality of patient population data subsets associated with different treatments of the identified defect; generating a visualization, comprising: a representation of each patient population data subset based on at least one patient characteristic; and a representation of the patient based on the at least one patient characteristic; and selecting a final treatment for the patient.

Other aspects provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 3 depicts an example of an anatomy measurement technique.

FIG. 4 depicts an example of an anatomy measurement technique.

FIG. 5 depicts an example for measuring parameters associated with bone loss.

FIG. 27 depicts an example method for classifying a defect with a statistical shape model.

FIG. 28 depicts an example decision support method.

FIG. 29 depicts an example method for determining a treatment for an anatomical defect.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
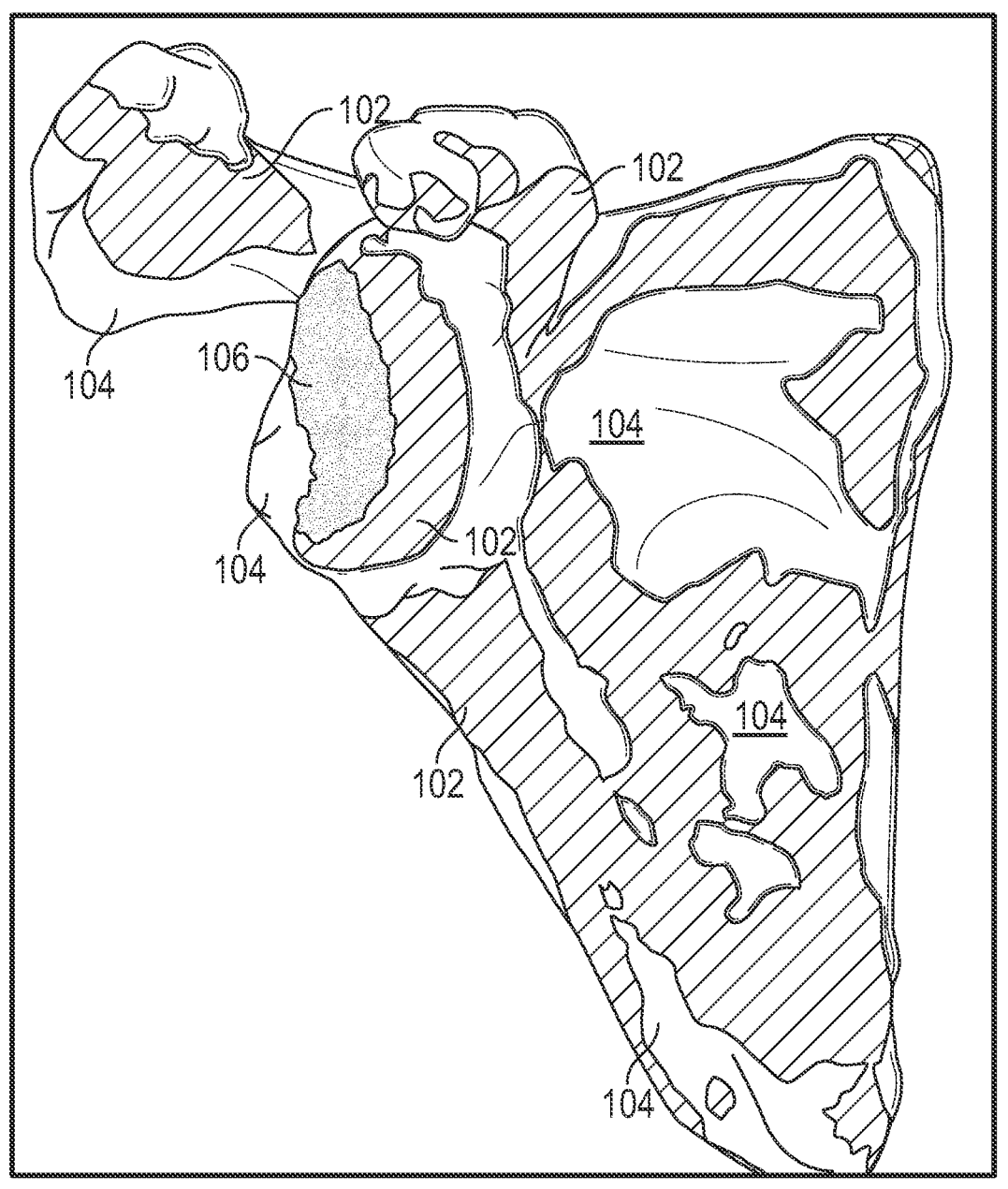
FIG. 1 depicts an example of a statistical shape model fitted to a 3D image of a patient anatomy.

Aspects of the present disclosure provide apparatuses, methods, processing systems, and computer readable mediums for surgery planning systems, including surgery planning systems with automated defect quantification and population-based decision support capabilities.

The surgery planning systems described herein resolve several problems with conventional surgery planning tools.

For example, conventional planning tools do not offer information on the healthy anatomy, and therefore do not allow a user to properly assess the size and location of the damage. The surgery planning tools described herein, by contrast, provide an automated defect classification system, which characterizes healthy anatomy as well as damaged anatomy. Thus, the surgery planning systems described herein overcome the issue of designing pre-operative plans based solely on damaged anatomy, such as bone and cartilage, among other things. Relatedly, the surgery planning systems described herein provide a better, more detailed, and automated visual representation of the damaged bone anatomy based on the defect classification.

As another example, while giving planning support for specific surgeries, conventional planning tools offer little support for choosing between such specific surgeries. The surgery planning systems described herein have a different starting point, allowing the user to also make more important, high-level surgical decisions. Thus, surgery planning systems described herein are more transparent to a user, such as a surgeon. Specifically, the surgery planning systems described herein provide statistical data allowing the surgeon to assess where the patient lies within a patient population, so that the surgeon can make informed decisions while creating a pre-operative plan. The transparency of the system allows the user to trace back every decision by providing the user with a complete patient profile. The surgery planning system also aims to reduce the number of manual interactions required for creating a pre-operative surgical plan.

The system and method disclosed in this invention consists of interconnected parts.

Defect Quantification and Classification

Embodiments of a defect quantification system may implement methods for computing characteristics of a defect or deformity in a patient's body, such as a bone, an organ, musculoskeletal regions, or any other anatomical part, using medical images as the starting point. In some embodiments, the defect quantification systems and method described herein may be a subsystem, module, or otherwise an integral part of a surgery planning system.

For example, the shape and size of a bone defect holds information that is useful to surgeons, implant or surgical instrument manufacturers, implant positioning software providers, educational institutions, and for patients, if needed. Many classification systems are used to describe the shape and size of bone defects, such as the Paprosky classification system for the hip, Dorr, Insall and Rand classification systems for the knee, Wallace, Walsch and Antuna classification systems for the shoulder, and others.

Conventional methods use qualitative measurements on standard radiography or two-dimensional (2D) computed tomography (CT) scans. They rely on the user visually identifying anatomical landmarks and guessing where a defect starts and what a regular, i.e. healthy, anatomy would look like. For example, in the case of a bone or cartilage defect, such as erosion of a glenoid, an acetabulum, a tibial plateau, a vertebra, craniomaxillofacial region, or any another bony anatomy or cartilage surface, existing techniques will have a user rely on anatomical landmarks or the observation of unusual bone geometry to assess which parts of the anatomy have eroded. However, without the shape of the undamaged anatomy as a reference, this generally cannot go beyond a mere assessment. Likewise, in the evaluation of soft tissue or organs, such as the heart, lungs, kidneys, brain, and others, under or overdeveloped parts, lobes, regions, chambers, vessels can be identified through visual assessment or rules of thumb, but without the shape of a normal or healthy anatomy as a reference, a truly meaningful quantification of such under or overdevelopment is not possible.

In addition, conventional methods use qualitative measurements based on 2D images. These measurements are not accurate as some information is lost in the conversion of 3D objects to their 2D representation. That is, the actual patient anatomy exists in 3D, but the images used to plan surgeries are captured in 2D. These 2D techniques have a poor reliability as a result of their qualitative nature and due to variations in the imaging protocols and circumstances. For example, the scale of objects in a 2D X-ray depends on the distances between the source and the acquisition plane and between the subject and the acquisition plane. Similarly, parallax effects also depend on those distances and on whether the source is static or moving. Further, the orientation of the patient with respect to the source and acquisition plane influences the projection of the anatomy.

In the systems described herein, a defect or deformity is measured from medical images of the patient using a model of a healthy body part as a reference (or as template). The size of the defect can be calculated in a number of ways by measuring distances between points or surfaces of the actual, damaged or deformed patient anatomy and the topological counterparts of such points or surfaces on the reference model. Distances can, for instance, be measured by projecting rays from a virtual model of the healthy anatomy and calculating the distance along those rays from the healthy body part to the damaged body part. A virtual model of the patient anatomy can be obtained by segmenting medical images of the actual patient anatomy. A virtual model of a corresponding healthy anatomy can be obtained in different ways, as is explained below. In order to allow the user to make a visual assessment of the damage or deformity, 2D or 3D virtual models of the damaged or deformed body part and the healthy body part may be superimposed and shown to the user. One or both of these models may be shown in a semi-transparent way.

The reference model of normal or healthy anatomy can come from different sources. For example, a mirror image of a healthy contralateral anatomical part may be used. To this end, medical images of said contralateral anatomical part may be segmented and the resulting virtual model mirrored.

In some embodiments, the methods disclosed herein use 3D statistical shape models (SSM) to make quantitative measurements and to predict the nature of deficiency defect or deformity by reconstructing the healthy body part. Statistical shape modeling may be used to predict the native, i.e. healthy, anatomical shape without requiring (images of) an actual healthy bone. In such embodiments, a virtual model of the healthy anatomy can be obtained by fitting an SSM of a healthy anatomy to parts of the (medical images or virtual model of the) patient anatomy.

Generally, an SSM is a mathematical model that represents the mean shape and shape variations within a population. Each shape generated by the SSM can be represented by a number of shape coefficients, which may be referred to as the SSM parameters.

In some embodiments, a method is performed on, for example, a 3D virtual model, 3D biomechanical model (musculoskeletal models), SSM, and/or SSM instance, so that there is no approximation or conversion of measurements between a 2D representation and the 3D world.

As an example, a fully automated defect classification system may be used for describing glenoid bone loss using three-dimensional measurements on scapula and/or humerus models and without needing a healthy contralateral reference scapula. In other embodiments, the automated defect classification system can likewise be used to measure defects or deformities in other body parts such as the heart, knee, hip, spine, foot, lungs, other joints, etc.

An example method may include: (1) acquiring medical image(s) of a patient with a glenoid bone defect or arthroplasty; (2) segmenting the scapula to obtain a virtual three-dimensional surface model, for example using Mimics by MATERIALISE®; and (3) fitting a statistical shape model (SSM) of healthy scapulae towards the healthy surface regions of the patient's scapula, as depicted in FIG. 1.

Keeping with this example, the SSM should describe the healthy scapula shape within the population to which the patient belongs. By fitting the SSM to the healthy portions of the patient's anatomy, the unhealthy surface (e.g., glenoid in this example) of the scapula will also be reconstructed. The shape correlations embedded in the SSM will produce a reconstructed glenoid that statistically has the highest chance of resembling what the original, healthy or native shape of the now unhealthy regions would have looked like.

Example SSM Fitted to Healthy Regions of Bone

FIG. 1 depicts an example of an SSM 102 fitted to the healthy regions of a scapula (e.g., 104) to reconstruct its original glenoid surface 106.

Different techniques may be used for fitting an SSM to partial data, such as healthy anatomy, so that the missing data (e.g., bone lost to bone erosion) can be predicted, such as posterior shape modelling. However, such techniques require an a priori identification of healthy and damaged or deformed areas. This step is known to exhibit a high inter- and intra-user variability. Accordingly, automating this step is beneficial.

Dividing SSMs into Regions for Improving Fit Error

Figure 2:
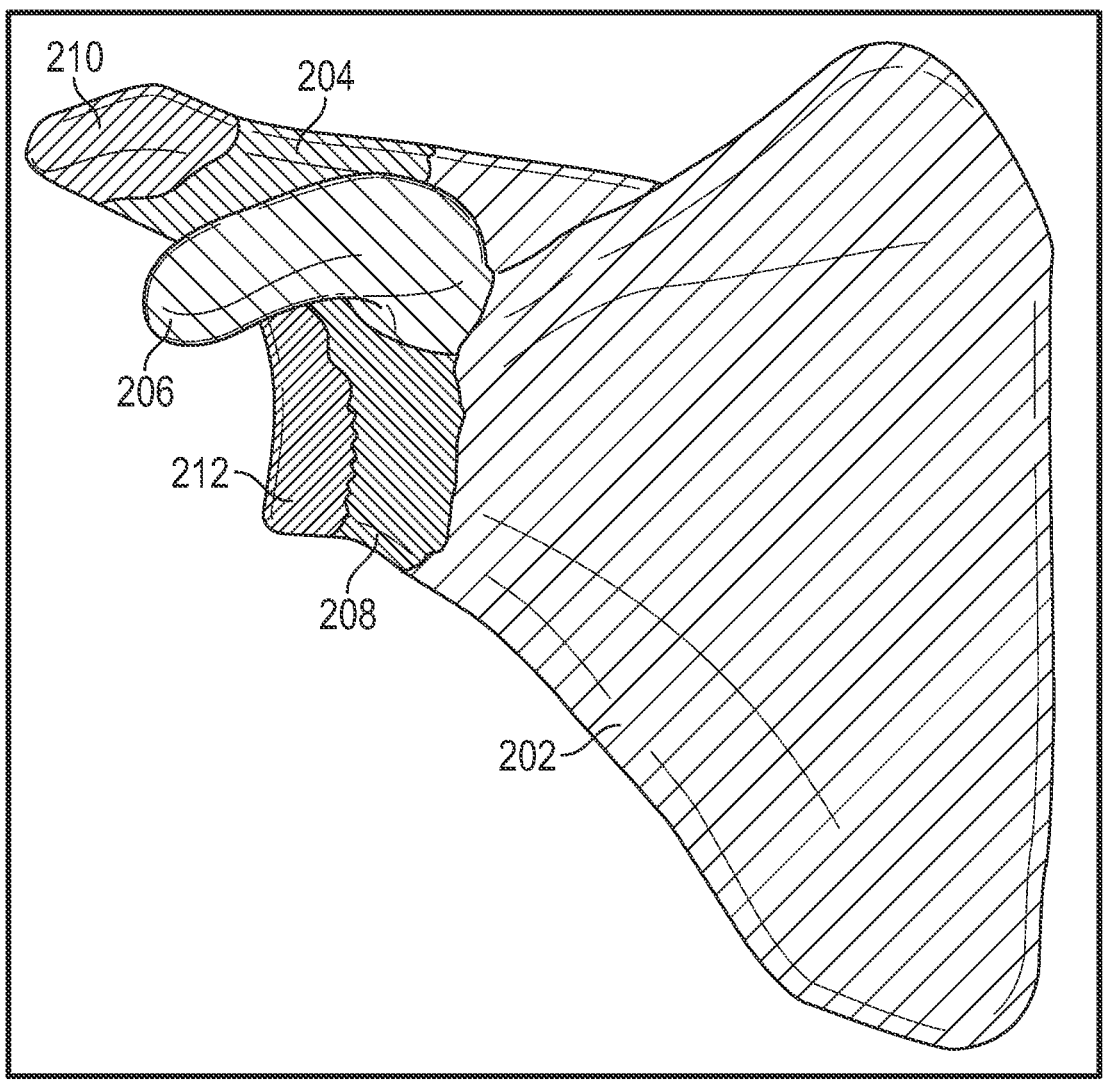
FIG. 2 depicts an example of a statistical shape model divided into six regions.

In one embodiment of an automated method, an SSM is subdivided in topological regions, such as regions 202-212 in the example of FIG. 2. For each of these regions, it is tested if including the region in the areas used for fitting the SSM results in a reduced or increased fit error. When including a certain region results in an unacceptable or increased fit error, the region is assumed to be damaged or deformed and is excluded from fitting. The SSM is subsequently fit to the subset of the remaining areas to obtain an SSM instance, representing what the anatomy of the patient would have looked like in healthy or non-deformed situation.

In the example of FIG. 2, the surface of an SSM representing a scapula is divided into six regions: base region 202, acromion region 204, coracoid region 206, neck region 208, acromion tip region 210 and glenoid region 212. This is just one example, and other subdivisions, such as subdivisions into different regions, or subdivisions into more or fewer regions, are possible.

Accordingly, an example method may proceed as follows. First, the SSM shape is fit to the target shape based on points in the base region 202 only. After convergence of the shape coefficients, the fit error is computed as the root mean square error (RMSE) between the points on the SSM shape used for fitting and identified corresponding points on the target shape.

If the fit error remains below a chosen threshold, a second fit is performed which uses points in the acromion region 204. If then the fit error exceeds the threshold, the acromion region 204 of the target shape is considered as non-healthy and the acromion region 204 is excluded from the subset of topological regions. The same selection procedure is subsequently repeated for points in the coracoid region 206, the acromion tip 210, and the neck region 208 in this example. In some cases, the glenoid region 212 may be expected to be eroded and thus not used for fitting.

If both the acromion region 204 and coracoid region 206 are excluded for fitting, for example based on fit errors exceeding a threshold, then in some cases, the acromion tip region 210 and neck region 208 are not further tested.

In various embodiments, different fit error thresholds may be used. For example, sensitivity studies have shown a fit error threshold of 1.7 mm to produce good results. Fit error thresholds of other values, such as 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.8 mm, 1.9 mm, 2.0 mm, 2.5 mm, 3.0 mm, to name a few, can also be chosen.

A similar approach can be applied to other anatomical structures. Thus, to generalize the process, an anatomical structure can be subdivided into a plurality of topological regions (e.g., 202-212 in FIG. 2). A first region (e.g., base region 202 in FIG. 2) may be selected to start the subset of topological regions, which in some cases may be a region remote from the defect or deformity. The first region may then be fitted and a fit error may be calculated and compared to a threshold, such as described above. Subsequently, additional topological region can be added to the subset, and the subset can then be fitted to the target model.

After each topological reason is added to the subset, the fit error can be recalculated and the additional topological region can be removed from the subset or kept in the subset depending on whether the fit error does or does not exceed a set threshold, such as the thresholds mentioned above. To speed up the process, topological regions that are not directly connected to the base region can be ignored if one or more regions in between are classified as damaged or deformed. To further speed up the process, and to improve results, topological regions that are known to be damaged or deformed can also be ignored.

Analyzing a bone defect (e.g., a glenoid bone defect) by comparing its shape with a predicted native shape (e.g., of an undamaged glenoid bone) results in quantitative measurements, such as, in the case of a glenoid bone, glenoid vault loss, glenoid vault loss percentage, glenoid erosion area, glenoid erosion area percentage, maximum erosion depth, and the like.

Distance Measuring Techniques for Comparing Anatomy Shapes

In one embodiment, in order to compare anatomy shapes (e.g., between predicted and actual shapes), distances can be measured between topologically equivalent points on models of each shape, such as between closest points, or between points along rays shot from one model to the other, to name a few options.

For example, for substantially spherical or hemispherical anatomical parts, such as the acetabulum 302 in FIG. 3, rays 304 may be shot in a concentric way from the center 306 of the sphere outwards, as depicted in the example of FIG. 3.

As another example, for substantially flat or planar anatomical parts, rays 404 may be shot in a parallel way, perpendicular to the best-fitting plane 402, such as depicted in FIG. 4.

As yet another example, for elongated anatomical parts, rays may be shot outwards and perpendicular to the central axis of the anatomical part. For other anatomical parts, rays may be shot perpendicular to the surface of the SSM instance. Notably, these are just a few options, and other ray-casting strategies or combinations of strategies are possible.

Thus, methods described herein may automatically compute metrics based on SSMs, such as: glenoid vault loss (the total volume of the glenoid vault lost due to bone erosion), glenoid vault loss percentage (the percentage of the volume of the glenoid vault lost due to bone erosion), local vault loss percentages (in superior, inferior, anterior and posterior region), erosion area (the surface area of the glenoid cavity affected by bone erosion), maximum erosion depth (the maximum distance measured between the actual anatomy surface and the healthy reference model), erosion area percentage (the percentage of surface area of the glenoid cavity affected by bone erosion), subluxation distance, and others. Notably, while a glenoid is used as in example herein, similar metrics may be calculated for other anatomical parts, such as other bones, joints, and the like. Based on this computation, the systems described herein may automatically classify a defect.

Example of Measuring Metrics Associated with Bone Loss

Using a glenoid bone as an example, the glenoid vault loss percentage metric indicates how much of the glenoid vault volume has been eroded and represents the severity of the glenoid bone defect. The superior, anterior, inferior and posterior vault loss percentages express how much of the vault has been eroded in each anatomical region or quadrant of the glenoid, giving a better understanding of the shape of the defect. The maximal erosion depth describes the amount of bone erosion at the deepest point of erosion. This measure can help surgeons to decide if they should ream or use bone graft during surgery. The erosion area percentage shows how much of the native glenoid surface is no longer intact, giving an indication on the amount of possible implant-bone support. Finally, the subluxation distance and region describe the amount and direction of humeral subluxation, which gives a better understanding of the cause of the glenoid bone defect.

FIG. 5 depicts an example for measuring metrics associated with bone loss in a glenoid bone.

To measure these metrics, a ray-casting algorithm (as described above) can be used. For example, first, a plane (e.g., 506) is fitted through the glenoid surface of the fitted SSM and parallel rays are cast from the glenoid points of the fitted SSM shape in the opposite direction of the plane normal. The distance at which a ray i intersects the fitted SSM shape is called the vault depth ($d_i^{vault}$) (e.g., 502), with $d^{max}$ (e.g., 504) as a chosen maximum value.

Then, the amount of bone erosion is assessed by shooting rays (e.g., 502 and 506) from the glenoid points of the fitted SSM shape towards the bone defect and parallel to the glenoid plane normal. The measured distances at which the rays intersect the bone defect is defined as the erosion depth ($d_i^{ero}$) (e.g., 506), being limited to $d^{max}$ (e.g., 504). If the erosion depth is infinite, there is simply no bone present at that location. Next, the loss depth ($d_i^{loss}$) is defined as the depth of the vault that is lost. The loss depth is similar to the erosion depth, except that it cannot exceed the vault depth.

Thus, in one example, for each ray i:

if $d_i^{vault} > d^{max}$: then $d_i^{vault} = d^{max}$ if $d_i^{ero} > d^{max}$ and $d_i^{ero} \neq inf$: then $d_i^{ero} = d^{max}$ if $d_i^{ero} \leq d_i^{vault}$: then $d_i^{loss} = d_i^{ero}$ if $d_i^{ero} > d_i^{vault}$: then $d_i^{loss} = d_i^{vault}$ Based on the depth measurements, the nine parameters that describe the glenoid bone defect can be computed.

For example, the vault volume is computed as the sum of all vault depths multiplied by the size of the corresponding surface elements ($A_i$). Similarly, the vault loss volume is computed as the sum of the loss depths, multiplied by the corresponding surface areas. Then, the vault loss percentage is calculated as the percentage of the vault loss volume compared to the vault volume.

For the superior (sup), anterior (ant), inferior (inf) and posterior (post) vault loss percentages, the glenoid surface is divided in four quadrants, using the glenoid center point. The vault loss percentages in these regions equal the local vault loss volume, divided by the local vault volume.

Next, in one example, the maximum erosion depth is computed as the 95-percentile value of all erosion depth values. The erosion area is computed as the area of all surface elements $A_i$ that encountered an erosion depth of more than one third of the maximum erosion depth. To obtain the erosion area percentage, in one example, the erosion area is divided by the total area of the glenoid. After projecting the humeral head center point to the glenoid plane, the subluxation distance is computed as the in-plane distance from the humeral head center point to the glenoid center point. The subluxation region is defined as the region (sup, ant, inf, post) on which the humeral head center point is projected on the glenoid.

Accordingly, in one example:

$$\text{vault volume} = \Sigma_i (d_i^{vault} \cdot A_i)$$

$$\text{vault loss volume} = \Sigma_i (d_i^{loss} \cdot A_i)$$

vault loss percentage=(vault loss volume)/(vault volume)

$$\text{local vault volume} = \Sigma_i (d_i^{vault} \cdot A_i) \text{ for all } i \text{ in region}$$

$$\text{local vault loss volume} = \Sigma_i (d_i^{loss} \cdot A_i), \text{ for all } i \text{ in region}$$

local vault loss percentage=(local vault loss volume)/(local vault volume)

$$\text{max erosion)depth} = p95(d_i^{ero})$$

$$\text{erosion area} = \Sigma_i A_i, \text{ for all } i \text{ with } d_i^{ero} > \frac{1}{3} \text{ max erosion depth}$$

$$\text{erosion area percentage} = (\text{erosion area})/(\Sigma_i A_i)$$

In some examples, multiple classification systems may be combined, such as the Wallace classification in the axial view and the Antuna classification in the frontal view (as above), which beneficially provides a user (e.g., a surgeon) a three-dimensional classification of the defect compared to the conventional two-dimensional classifications.

Notably, similar quantification can be performed on other anatomical parts, such as other joints, other bones, organs (heart, lungs, kidneys, brain, and others) to evaluate damage, deformity, or disease. Based on this quantification, similar classification systems can be defined. The system and the method uses an appropriate and/or known classification system or combinations thereof, based on the body part that requires treatment.

Pre-Operative Surgery Planning Tools

Existing pre-operative planning tools, such as the Surgi-Case Knee Planner by MATERIALISE®, offer the possibility of generating a pre-operative surgical plan for a specific type of surgery (generally involving a specific type, brand, or product line of implants). Pre-operative planning generally starts after important surgical decisions have been made by a surgeon, such as: type of surgical treatment, type of implant and type of surgical instruments to be used, standard implant versus patient-matched, etc.

Further, these decisions are based on medical images taken from the patient. For orthopedic treatments, for example, those medical images may depict damaged bone/cartilage anatomy. Existing planners generate an initial or default plan based on the damaged anatomy (e.g., bone and/or cartilage), which is then reviewed by the surgeon. Upon review, the surgeon may propose certain changes, such as: position or size of the implant, that are then incorporated by the planner and a new pre-operative plan is generated for use during the actual surgical procedure.

Unfortunately, as existing planners only take medical images as input, the pre-operative plan only takes information into account that is visible in those medical images. The pre-operative plan does not address any aspects that cannot be readily derived from the medical images or all the complexities associated with the surgery that a surgeon encounters in an operating room, which might affect the surgical outcome, the risk of intra-operative or post-operative complications, or patient satisfaction.

A surgical planning system may use more than patient-specific medical images by using an aggregate prediction technique that is based on one or more known pre-operative plan sets. For example, such a planning system may source historical data from pre-operative plans, data gathered intra-op, and data gathered post-op. Further, the planning system may select pre-operative plans into a pre-operative plan set and then apply prediction techniques, such as machine learning, deep learning, neural networks, or other artificial intelligence (AI)-based techniques, to create aggregate pre-operative plans and suggest changes to a user. However, this method of pre-operative plan generation is generally not transparent to the surgeon, i.e. the surgeon does not know how or why the planner incorporated the proposed changes, which characteristics of the particular patient lead to the suggested changes, how sensitive the system is to those characteristics, or the impact of those changes on the patient beforehand. Thus, while the system itself may be self-learning, it does not allow the surgeon to make informed decisions.

The systems disclosed herein overcome the drawbacks of existing surgical planning tools by providing a surgeon with more information and serving as a guide to the surgeon. As a guide, embodiments of the systems described herein provide timely suggestions, advice, and warnings along with detailed information substantiating such suggestions, advice and warnings, allowing a surgeon to make informed decisions. The control of the system lies with the surgeon such that the surgeon can consciously make every decision, making it a transparent and user-friendly system. The systems disclosed herein beneficially reduce the time spent in the operating room and the changes that the surgeon has to address in the operating room, and increase the likelihood of a positive surgery outcome, thus overall reducing the number of revision surgeries that a patient may need.

Systems described herein may use multiple feedback loops to provide information to the surgeon by way of suggestions, warnings, advice and/or default pre-operative plans which also involve establishment of one or more interconnected databases.

Surgical Planning Workflows

Surgical planning methods (e.g., performed by surgical planning systems described herein), may include a plurality of steps, including: (1) loading medical images; (2) processing the medical images, for example to identify anatomical landmarks and/or create one or more virtual 3D models of the anatomy; (3) automatically creating a default surgical plan, which is generally based on a number of geometric calculations based on the identified landmarks and typically comprises a selection of one or more implants, implant sizes, locations and orientations for all implants, the corresponding resections or reaming steps, etc.; (4) allowing the clinician to alter the default plan to obtain an approved pre-op plan; and (5) making the pre-op plan available for execution in surgery. In some embodiments, the pre-op plan can, for example be used in a navigation system, a robotics system, to design patient-specific guides, in augmented and/or virtual reality systems, and for other purposes.

Figure 6:
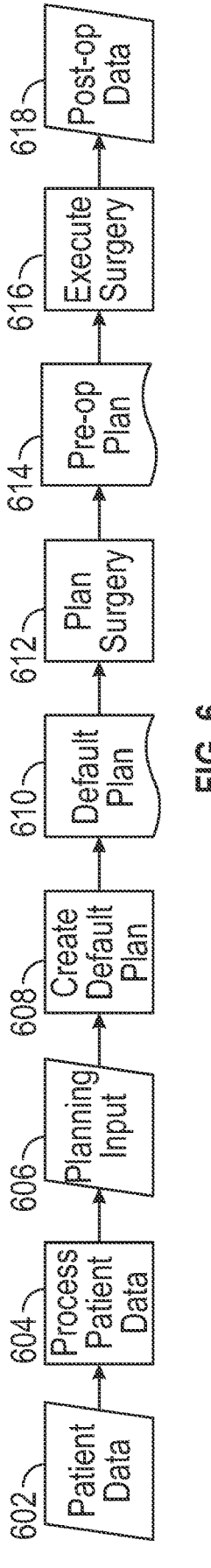
FIG. 6 depicts an example of a surgical planning workflow.

For example, FIG. 6 depicts a workflow of conventional surgical planning methods and tools including steps 602-618.

A database or other data store may be used to store the approved plans together with related patient data, such as the medical images and any virtual 3D models and landmark information in a database. Additionally, the systems described herein add one or more feedback loops to the workflow depicted in FIG. 6.

Figure 7:
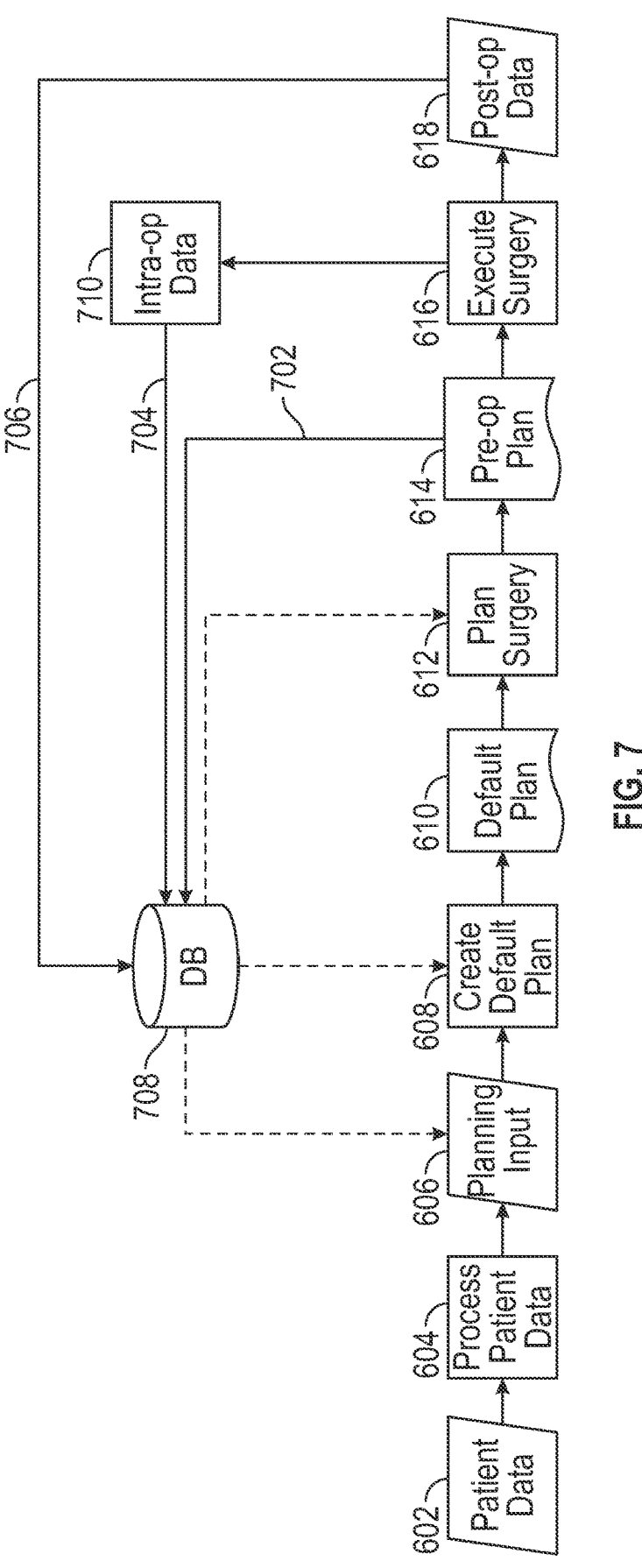
FIG. 7 depicts another example of a surgical planning workflow.

For example, a first feedback loop 702, as depicted in FIG. 7, may mine information from the approved pre-op surgical plans for use before or in the planning step and store it in a database 708. A second feedback loop 704 may gather information intra-operatively, store the data in the database 708, and mine that information for use before or in the planning step. A third feedback loop 706 may gather information post-operatively, store the data in the database 708, and mine that information for use before or in the planning step.

Figure 8:
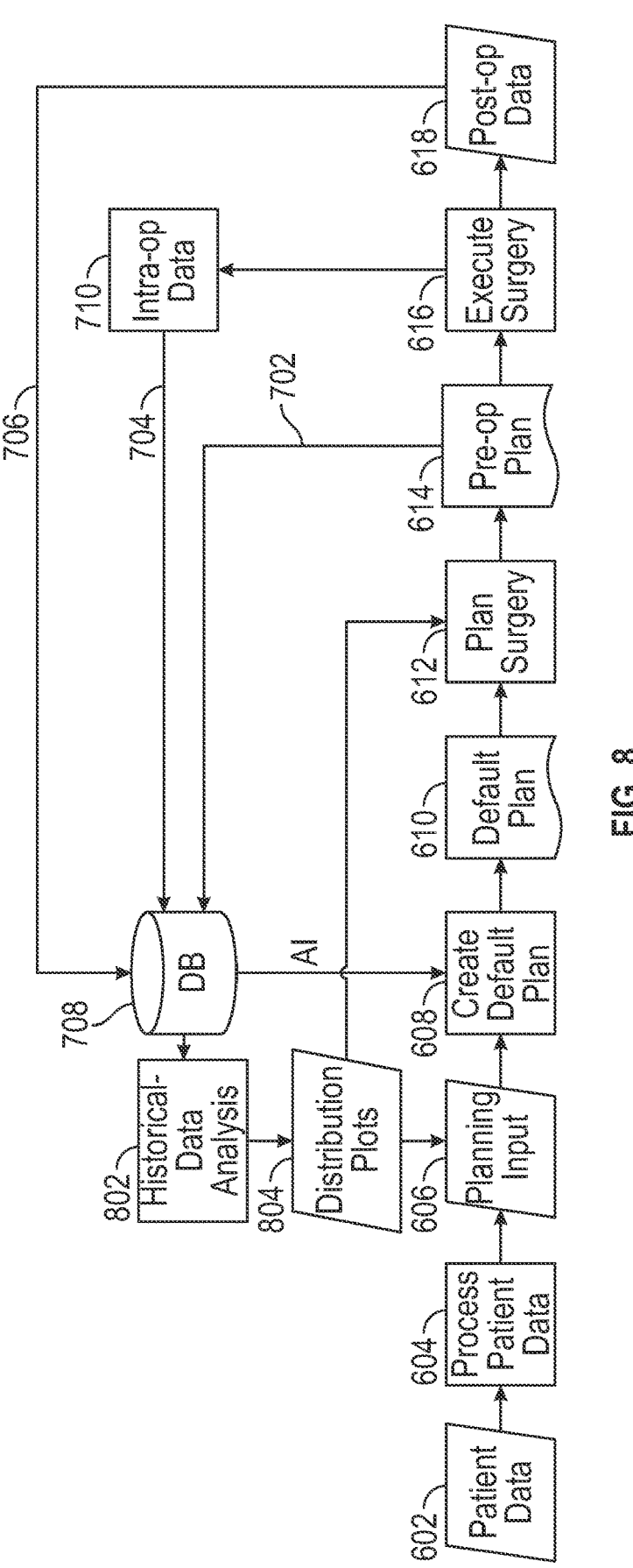
FIG. 8 depicts another example of a surgical planning workflow.

A further improvement to the data flow described in FIGS. 6 and 7 is shown in FIG. 8, wherein the historical data available in the database is used to perform a historical-data analysis 802, relating either patient characteristics to planning decisions, or one or more planning parameters to surgery outcomes. Further, the results of this historical-data analysis may be presented to a user (e.g., a surgeon) in such a way that the location of the patient within the population or the planning parameters are shown together with the distribution of the planning decisions or surgery outcome, respectively, over the population (e.g., at 804). Beneficially, presenting this information does not force the user to blindly choose between accepting and declining a suggested plan alteration. Rather, it shows the user what planning decision options or parameter values are appropriate and to what degree they are more appropriate than other options or values with the possible post-op scenarios.

For example, when considering options A, B, and C, the system does not simply suggest: "Take option A", but may show how the patient population is distributed over options A, B, and C and where the patient lies within the population. From the representation of the results of the historical-data analysis, the user can not only see if the patient sits squarely in option A, or rather on the border between options A and B, but also whether that border is a sharply defined one or rather a broad range with a smooth transition.

Surgical Planning Data and Databases

Systems described herein may utilize one or more databases, which are connected to different parts of the surgical planning system via one or more feedback loops. For example, data may be collected at one or more stages of the workflow, as described above with respect to FIG. 7, and stored in a database.

In some implementations, the data collected may be divided (logically or physically) into subsets, such as patient data, pre-operative data, including collection of pre-existing plans (i.e. already used pre-operative plans for future pre-operative plan optimization), retrospective data, intra-operative data, and post-operative data. Links between data in different subsets but related to an individual patient are maintained; in other words, the database keeps track of which patient data, pre-operative plans, intra-operative data and post-operative data belong to the same patient. As above, the data may be stored in a single database or in different databases.

Which of these types of data is stored in the database(s) depends on which feedback loops are implemented in the system. Some subset of patient data is always stored. However, a basic system may, for example, only implement the feedback loop of approved pre-op plans. Other systems may also implement the feedback loops of the intra-operative data and/or the post-operative data. Other combinations are possible. One or more feedback loops may be invoked at a certain time. In some embodiments, in case of revision surgeries, all feedback loops may be invoked to get the entire patient profiled from previous surgeries.

In some embodiments, the systems described herein may run locally or "on-premises", in which case the database(s) may contain only data relating to one or more local users, such as surgeons, physicians, or clinicians or their teams. In other embodiments, the system may be a network-based system, such as a web-based system or a cloud-based system, in which case the database(s) may contain data relating to a larger user base.

Patient data may be stored in the form of one or more of medical images, personal information, such as age, sex, weight, height, ethnicity, lifestyle, activity level, medical history, and any data gathered during pre-surgical exams, such as complaints, pain scores, gait measurements, range-of-motion measurements, degenerative or congenital defects, sports or age-related injuries, genetic information, dental casts, and others. In some embodiments, patient data may be anonymized to protect patient privacy or to comply with various patient privacy regimes, such as the Health Insurance Portability and Accountability Act (HIPAA) or General Data Protection Regulations (GDPR).

Pre-operative data may be stored, for example, in the form of pre-operative treatment plans (e.g., 614 in FIGS. 6-8), which may be alternatively referred to as pre-op plans or pre-op surgical plans. Pre-operative data may capture some or all medical decisions related to treatment of a patient's medical condition, such as one or more of: type of treatment (both invasive and non-invasive treatment); types, brands, product lines, sizes, implantation locations and orientations of planned implants, if any; delivery systems and approaches of any implants; designs of patient-specific instruments, if any; details of any reaming steps; types or designs of any defect-filling components, such as autografts, allografts, porous structures, and other aspects.

Intra-operative data (e.g., 710 in FIGS. 7-8) may be stored in the form of any data captured during surgery, such as measurements, the locations of intra-operatively identified anatomical landmarks, observations, or the occurrence of intra-operative complications. The intra-operative data may relate to information that cannot be easily derived from medical images or pre-surgical exams, such as information relating to soft tissue, muscles, muscle attachment points, muscle ruptures, tendons, ligaments, ligament tension, etc. Intra-operative data may also comprise any changes made during surgery with respect to the pre-op plan. Intra-operative data may also include synthetic data, which in one example, may be data that cannot be quantified but can be noted down due to its influence on surgery outcome such as ligament forces in case of knee. This may be stored in the form of biomechanical models.

Post-operative data (e.g., 618 in FIGS. 6-8) may be stored in the form of any data captured after surgery, such as the occurrence of any complications, any data captured during post-surgery exams, pain scores, patient satisfaction, functional scores, revision surgery, post-surgery imaging, recovery time, rehabilitation time, rehabilitation method of treatment, details and observations of the physiotherapist; if any, range of motion measurements, and the like.

Data may be entered into the system either manually or automatically through the surgical planning system, through any devices used during surgery, such as navigation systems, robotics systems, or augmented reality (AR) or virtual reality (VR) systems, through an electronic access device, through wearable devices, or through sensors embedded in implants or chips embedded in the patients. Notably, these are just a few examples.

The example surgery planning systems described herein may implement the automated defect quantification system discussed above. Based on the defect classification and description, the surgery planner provides additional valuable information to the surgeon to help plan and execute the surgery.

Acquisition of Patient Data

Patient data may be loaded from a file, storage medium or database or entered manually into the system. If the patient has previously undergone surgery, his old file may be recalled from the database. If not, a new case file or record is generated.

For many applications, medical images will be a valuable part of the patient data.

Data processing: Patient data may be processed. For example, medical images may be converted into one or more virtual 3D models of anatomy parts, such as bony anatomy, cartilage, organs, organ walls, blood pool volume, and others. Anatomical landmarks may be determined or indicated in the medical images or in the virtual 3D models. This may be done manually or automatically, e.g. by means of feature-recognition techniques. Further information may be derived from the medical images, such as bone density information, bone loss, impingement of bone-to-bone contact, spread/extent of the defect on the surrounding anatomy, adjoining and attached soft-tissue characteristics such as muscles, ligaments, cartilage, tendons, meniscus, thickness of soft tissues, etc. Additionally, biomechanical models may also be generated to demonstrate musculoskeletal data such as bony anatomy along with soft-tissue data that may be further simulated.

In some embodiments, defects or deformities are quantified and/or classified as described above.

Default Treatment Plan Creation

In some embodiments, surgical planning systems as described herein may be related to a specific surgery and/or to a specific type, brand or product line of implants. Additionally, unlike conventional systems, the systems described herein may support more important, higher-level treatment decisions, such as: type of treatment, including invasive treatment, non-invasive treatment, or referral. Further treatment decisions may include type of implant since many pathologies can be treated with different types of implants, such as off-the-shelf, customized, or custom implants or combinations thereof. For example, for joints: cartilage repair, resurfacing, or replacement; partial or total (e.g. unicondylar/total distal femur implant, unicompartmental/total proximal tibia implant); fixation strategy (cemented/non-cemented, stemmed/stemless, press fit, screws); functional strategy posterior-stabilized/cruciate-retaining femur implant, anatomical/reversed shoulder implant); acceptable range of motion; and others may be considered. For cardiac applications: valve repair, stapling, replacement, ring annuloplasty, type of stent, and others aspects may be considered. For craniomaxillofacial applications: orthognathic, reconstructive, trauma, TMJ, dental alveolar type of surgical procedures, treatment of maxilla or mandible or both, orbital floor, or parts of the cranium, and other relevant aspects may be considered.

For pulmonary applications: intraluminal and extraluminal stent, type of valve, and other aspects may be considered.

For type of instrumentation or guidance: conventional instrumentation, patient-specific guides, navigation systems, AR system, robotics systems, and others may be considered.

To support these decisions, the surgeon may be presented with additional relevant information to understand the defect in more detail, such as the information or models derived from the medical images and/or the results of the defect or deformity quantification and classification as described above. For example, the surgeon may be presented with the results of the quantification and classification, and/or with a visual representation of the defect or deformity by means of a superposition of a virtual 3D model of the actual patient anatomy and a model representative of healthy anatomy, such as from fitting an SSM to parts of the patient anatomy. One or more models may be shown in a semi-transparent way, such as described above. A biomechanical model simulation may also be shown alongside the virtual 3D SSM model.

As a further support for these decisions, the system may run one or more population analyses based on the historical data gathered in the database through the one or more feedback loops. Such an analysis may relate one or more patient characteristics to one or more of the treatment decisions. Thus, the system may utilize 1) a selection of a population, 2) a selection of a treatment decision to support and 3) a selection of one or more patient characteristics to characterize the members of the population and the patient to be treated. These selections may be left to the user, for example by means of drop-down boxes or check boxes in a user interface. Alternatively, the system may present the user with one or more pre-programmed combinations of selections, for example in a wizard-style process. Correlation analyses may reveal which patient characteristics may be relevant for which treatment decisions. Alternatively, the system may first track user behavior and subsequently present the most common combinations by default. For example, an AI-based system may learn about the frequently chosen decision influencers and during future pre-operative planning stages, display them to the surgeon at appropriate times. Alternatively, an AI-based system may learn the correlation between certain characteristics, notably 'best characteristics' and their influence on treatment decisions and use them to optimize and thereby provide treatment options based on 'best' characteristics or based on surgeon's preference of "best characteristics."

Regarding the selection of a population, a historical-data analysis may be based on all records in the database or on a subset of records. For example, the population may be limited to only those records that are complete enough, i.e. records that contain the appropriate data needed for the analysis. The population may also be limited to patients that have one or more characteristics in common with the patient to be treated, e.g., sex, age, ethnicity, and others. The population may also be limited to only those patients that have been treated in the same country, in the same hospital or by the same clinician, physician, surgeon, school of thought, or the like.

The historical-data analysis may reveal how the selected population is distributed over the different options for a selected treatment decision. The members of the population are characterized by means of the selected patient characteristic(s). The patient to be treated may be positioned through his/her specific patient characteristic(s) within the analyzed population, so that it may be revealed which decision option, according to the historical data in the database, would seem the most appropriate for this particular patient. Alternatively, at the same instance, the system may show a comparative analysis based on the system chosen "best" characteristic(s), if it differs from the selected patient characteristic(s), thereby allowing the user to re-evaluate his decision.

In some embodiments, the historical-data analysis may relate one or more treatment decisions to an expected occurrence of an intra-operative or post-operative event, observation, or outcome. The historical-data analysis may, for instance, reveal how the chance or risk of a certain event, observation or outcome happening increases or decreases with a certain pre-operative plan parameter.

For example, the historical-data analysis may relate the chosen size of a heart valve with the risk of leakage, or may relate a chosen amount of lateralization of a shoulder implant with the risk of acromion fracture.

In certain embodiments, the historical-data analysis may make use of retrospective data containing data acquired from high-level surgeons or key opinion leaders (KOLs) and provide it to new or low-level surgeons to guide their decisions such as bone defect data, mimicking the treatment options or providing their used or preferred treatment plans to low-level surgeons. In some embodiments, retrospective data may contain information provided and used by a school of thought (e.g., surgeons using the same plan or treatment options or other aspects).

This type of analysis can be made more accurate or more relevant to the patient to be treated by limiting the population to those patients that show a similarity to the patient to be treated, for example regarding one or more patient characteristics. This type of historical-data analysis may require: 1) a selection of zero or more patient characteristics to limit the population; 2) a selection of one or more types of events, observations or outcomes; and 3) a selection of one or more treatment decisions. As before, these selections may be left to the user, for example through drop-down boxes or check boxes in the user interface. Alternatively, the system may present the user with one or more pre-programmed combinations of selections, for example in a wizard-style process. Correlation analyses may reveal which events, observations or outcomes may be relevant for which treatment decisions. Alternatively, the system may first track user behavior and subsequently present the most common combinations by default. For example, an AI-based system may learn about the frequently chosen decision influencers and during future pre-operative planning stages, display them to the surgeon at appropriate times.

Regarding the selection criteria of the population, the population should preferably be limited to members that show a similarity to the patient to be treated. This similarity can relate to one or more patient characteristics.

For example, in the case of heart-valve leakage, those patient characteristics can be a set of measurements describing the shape of the anatomy surrounding the valve, such as smallest and largest diameter of the annulus.

As another example, in the case of acromion fracture, the patient characteristics can include information regarding bone density as derived from a CT scan or the results from the defect quantification and classification described above.

For those analyses where the result is known or suspected to depend on the shape of the patient anatomy, the patient characteristics can include the parameters or a subset of the parameters of an SSM fit to a part of the patient's anatomy. These parameters or such a subset form an n-dimensional vector describing the patient's shape in an n-dimensional space encompassing all possible shape variations. The population for the historical-data analysis may therefore be limited to all members whose corresponding n-dimensional vectors fall within a certain pre-set distance from the patient to be treated.

The results of the historical-data analysis may be presented in different ways, some examples of which are described below. Example embodiments of population analyses are also described below.

As an alternative to a historical-data analysis, the system may also locate within a selected population the member that most closely matches the patient characteristics of the patient to be treated and display the decision options chosen for that member.

Once the high-level treatment decisions have been made, either with or without the use of a decision-support process as described above, the systems described herein may create a default pre-operative plan for the patient to be treated. This plan will typically rely on one or more algorithms or heuristics that compute treatment parameters, such as: implant position and orientation, based on patient data and processed patient data.

For example, the SurgiCase Knee Planner uses a geometric algorithm based on anatomical landmarks identified on virtual 3D models of a patient's femur and tibia to compute local anatomical coordinate systems, and default sizes, locations and orientations with respect to the patient anatomy of a femur implant and a tibia implant. For certain input parameters of such algorithms, general, population-wide values may be utilized. Alternatively, values may be chosen—manually or automatically—based on support from decision-support processes as described above.

For example, for total knee arthroplasty, a default value of varus correction to 3° varus may be used for all patients, a historical-data analysis may suggest a certain value for the varus correction, or the value for the varus correction of the closest-matching member of the population may be used. Thus, the decision-support processes of the present invention may be used both for high-level treatment decision and for lower-level, treatment-specific decisions.

The historical data gathered through the one or more feedback loops may also be used to improve automatically created default plans or to create new, default plans. For example, AI-based techniques, such as machine learning, deep learning, neural networks and the like, may be used to incorporate changes that are often or consistently made in the planning step or during treatment into the default plans. In addition, information about intra-operative or post-operative complications may be used to include some changes and ignore other changes.

Modifying Treatment Plans

Once a default plan has been made, it is presented to a user for further fine tuning. The user may be presented with the possibility of altering one or more treatment plan parameters. For example, the user may have the possibility to change an implant size, an implant location or implant orientation.

In the planning step, the system may support the decisions of the user by means of the decision-support processes described above.

The result of the planning step is an approved pre-operative plan, i.e. a treatment plan that the clinician has decided to execute.

In some embodiments, the system includes a feedback loop storing all approved pre-operative plans in the database. The information gathered in this way can be used as historical data to feed the decision-support processes. For example, running population analyses on the approved pre-operative plans of the user will tell the user what changes or parameter values lie within his past practice or experience. In contrast, running population analyses on the approved pre-operative plans of all users will allow the user to learn from the accumulated experience of a much larger group of people, or to compare his personal practice to the average practice of all users. Other options are possible, such as limiting the historical data to the approved pre-operative plans of all users of the same hospital, or all users of the same country.

Patient Treatment According to a Treatment Plan

Once an approved pre-operative plan has been made, the clinician may proceed to its execution, i.e. treating the patient. In some—mainly non-invasive—treatments, the pre-approved treatment plan may take the form of a prescription, such as for medication or exercise. In other—mainly invasive—treatments, the pre-approved treatment plan may take the form of a data file that may be used in a surgical guidance system. For example, the plan may be used to design and manufacture patient-specific instruments that help a surgeon realize a planned surgical outcome during surgery. Alternatively, the plan may be loaded into a surgical navigation system or an AR system to display guidance information to the surgeon during surgery. Alternatively, the plan may be loaded into a robotics system, to automatically or semi-automatically execute part of the surgery.

The system may comprise a feedback loop to store intra-operative data in the database. This may comprise any of the aforementioned intra-operative data. The data can be gathered automatically by means of sensors in the operating room, by means of specialized surgical equipment, by means of surgical guidance systems, such as navigation systems, AR systems or robotics systems, or can be entered manually through an electronic access device.

For example, the system may prompt the surgeon to store any intra-operative changes or complexities encountered during the surgery. This information can be about implants, the surrounding patient anatomy, the actual implant and surgical instrument used, synthetic data that cannot be measured but is vital, etc. The system may also act as a notebook for the surgeon to note down any relevant information about the patient anatomy which may be useful at a later stage. This data is stored in the database for two purposes: 1) to complete the patient case file; and 2) to optimize future pre-operative plans.

The information gathered in this way can be used as historical data to feed the decision-support processes described above. For example, capturing intra-operative measurements and observations allows presenting statistical information to the user in the steps before approving the pre-op plan about patient characteristics that cannot be deduced from the available medical images or can only be measured in an invasive way, such as ligament tension, the occurrence of infections or damage to soft tissues, etc. As another example, capturing information regarding intra-operative complications allows presenting statistical information to the user in the steps before approving the pre-op plan about the likelihood of such complications. Finally, capturing any changes made to the operative plan, or any departures from the approved pre-op plan allows replacing or extending the decision-support process described under "Planning step" from presenting information about choices being made during the planning steps to choices being made during surgery.

Post Treatment Data Gathering

After the treatment, more information may be gathered and captured through a feedback loop, such as post-operative medical images, virtual 3D models based on such images, post-operative measurements, functional measurements, pain scores, functional scores, patient satisfaction information, information about post-operative complications, activity data, information about revision surgery . . . . The data can be gathered automatically, for example by sensors embedded in one or more implants or wearable devices, or entered manually in an electronic access device.

The information gathered in this way can be used as historical data to feed the decision-support processes described above. For example, it allows presenting statistical information to the user in the steps before approving the pre-op plan about actual surgical outcome, potential complication risks, implant life expectancy or patient satisfaction.

Ineffective Treatment Plan Elimination

A special form of intra-operative or post-operative feedback loop gathers intra-operative and post-operative information regarding complications and uses it to classify, tag or flag less effective pre-op plans, for example based on how much the execution of the surgery diverted from the pre-op plan based on certain threshold (may be user-defined), on the severity of the complications or the life span of an implant. This feedback loop allows further optimizing automatically created default plans by eliminating the least effective treatment plans from the training data for AI-based techniques generating such default plans. This feedback loop also allows improving the decision support systems by eliminating the least effective treatment plans from the data used in historical-data analyses.

A very basic form of elimination feedback loop allows the user to manually flag pre-op plans or treatment plans that should not be included in any training data or historical-data analyses.

Presenting Results of Historical Data Analysis

The information generated as part of the decision-support processes may be presented to the user in any practical way. For example, when supporting a decision involving a limited number of discrete options or discrete parameter values—such as the choice between a number of treatment options or available implant sizes—distribution graphs or histograms may be shown for each of these options with one patient characteristic as independent variable. The value of the patient characteristic for the specific patient to be treated may be indicated on the graph by means of a mark on the independent axis, so as to show to the user which decision option seems most appropriate for the patient based on historical data.

Figure 9:
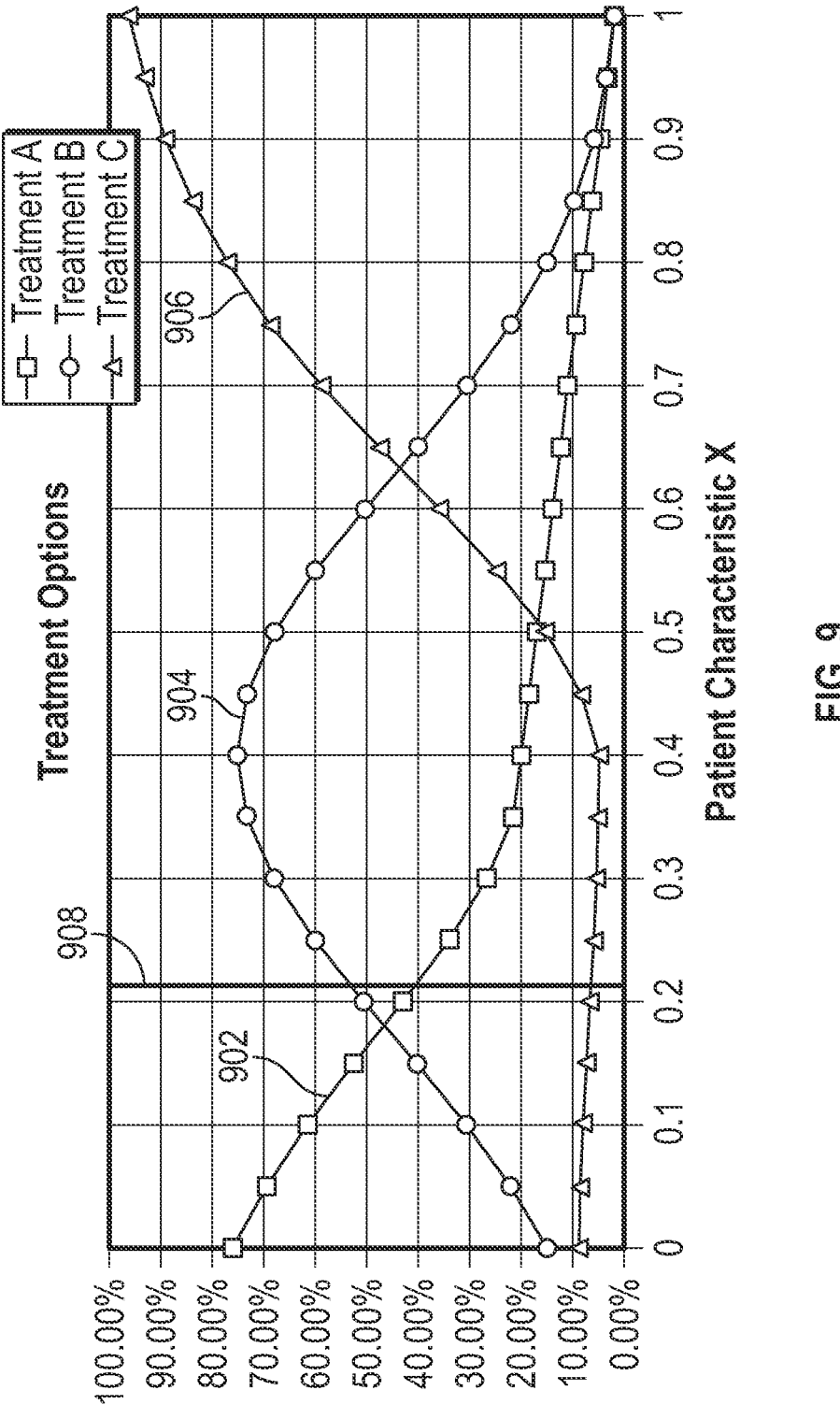
FIG. 9 depicts an example of a historical data-based analysis of patient populations for assessing treatment options.

For example, FIG. 9 depicts an example of results of historical-data analysis represented in the form of distribution plots 902-906. The location of the patient to be treated within the patient population is indicated by the vertical line 908. From this the user may derive that Treatment B seems most appropriate.

This represents an important improvement over conventional systems that merely present the user with suggestions for discrete treatment options or discrete parameter values. For example, in FIG. 9, the results of a historical-data analysis are presented to the user, preferably in an intuitive way. Specifically, in FIG. 9, the user does not just get the suggestion "Treatment B". The user also sees where the patient lies within the patient population, and whether there are sharp or smooth transitions between different options. For example, the user can derive from the graph that Treatment B seems most appropriate, but also that Treatment A might be a likely contender and Treatment C is not. If the surgeon has other medical or non-medical reasons to prefer Treatment A over Treatment B, such as treatment cost or his own lack of experience with Treatment B, the system of the present invention would not simply suggest Treatment B, but also teach the user that Treatment A is a viable option and subsequently provide the user with all the relevant information for Treatment A.

Alternative representations are possible. For example, the data of the graph above may also be shown as area or bar charts. Alternatively, it may be shown in a gradient (e.g., color gradient) plot, where each of the decision options is represented by a particular color, pattern, or intensity (e.g., a greyscale) and the distribution of the population over the decision options is represented by mixing proportionate amounts of the respective colors, patterns, or intensities.

Figure 10:
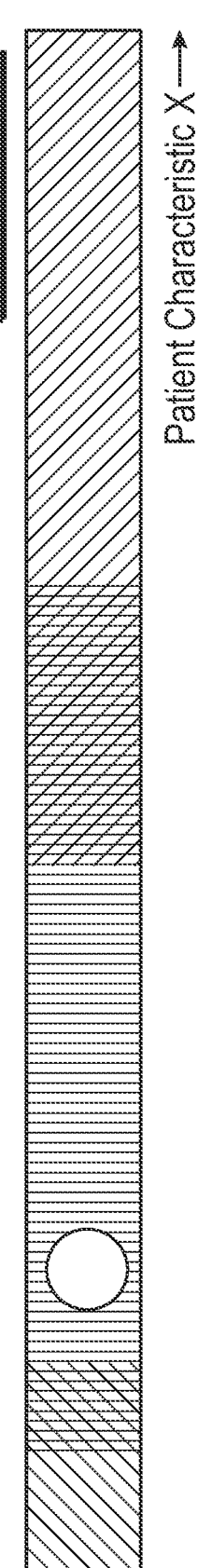
FIG. 10 depicts an example of a historical data-based analysis of patient populations for assessing treatment options.

For example, FIG. 10 depicts an example of results of historical-data analysis represented in the form of a color plot. The location of the patient to be treated within the patient population is indicated by a white dot. From this the user may derive that Treatment B seems most appropriate.

From the plot in FIG. 10, a user may derive similar information as from the distribution graphs described above. Specifically, the user may derive the patient's location within the population, how the population is distributed over different treatment options or parameter values and, by looking at the color gradients, whether there are smooth or sharp transitions between those options and values. It may be harder to derive numerical values from a color plot, but a color plot may be more intuitive to interpret.

In other embodiments, analyses relating discrete options to two patient characteristics may be presented by other visual means, such as 3D bar graphs or other 2D plots (e.g., using colors, patterns, intensities, or other visual references).

As another example, the results of a historical-data analysis supporting the choice of a continuous-value parameter—such as varus correction for a knee implant, lateralization of a shoulder implant, implantation depth of a heart valve or a patient satisfaction score—can be presented by means of a line graph.

Figure 11:
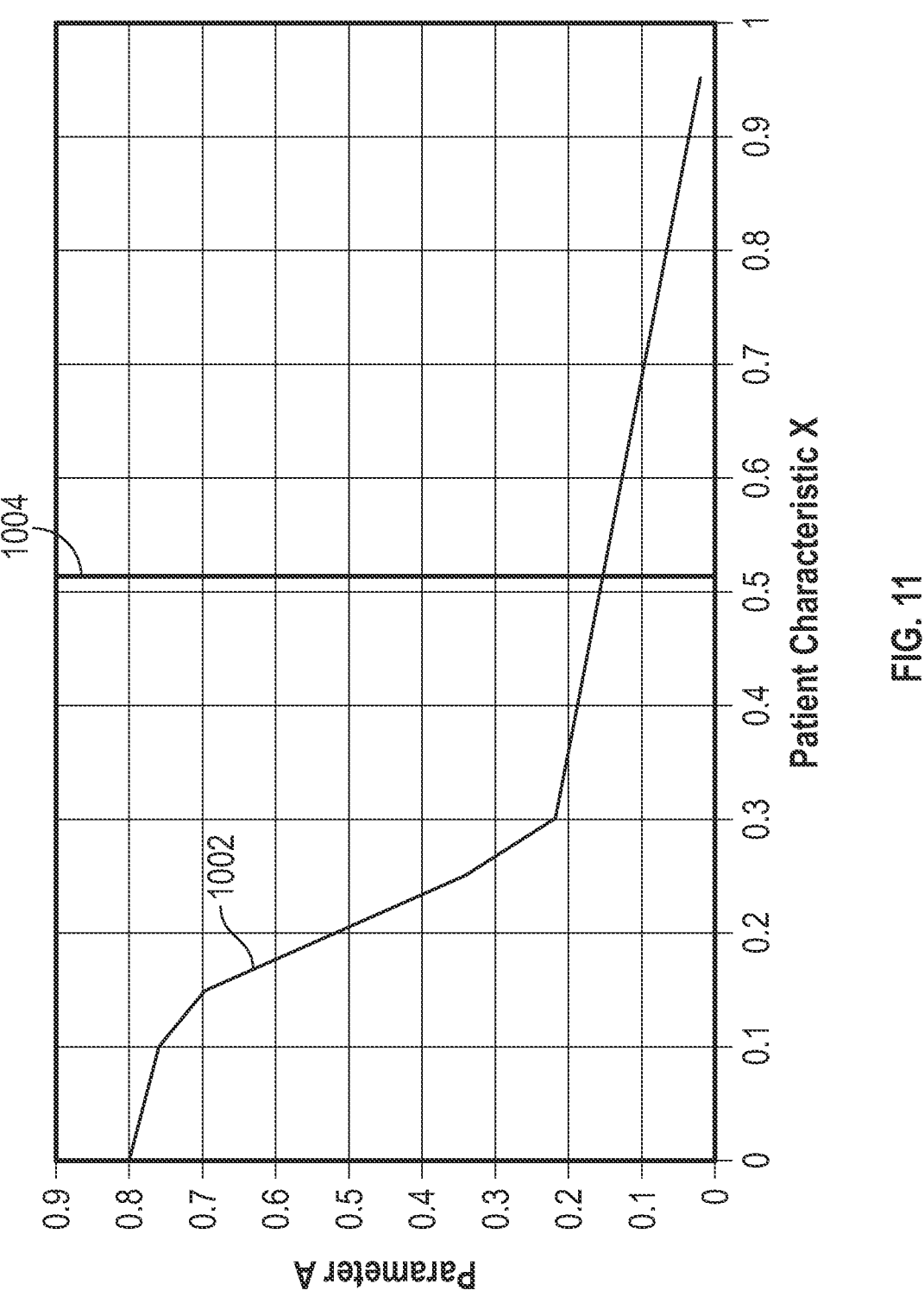
FIG. 11 depicts an example of a historical data-based analysis of patient populations for assessing a parameter value.

For example, FIG. 11 depicts an example of results of historical-data analysis represented in the form of a line plot 1002. The location of the patient to be treated within the patient population is indicated by a vertical line 1004. From this the user may derive that a value between 0.1 and 0.2 for Parameter A seems most appropriate.

Examples, such as FIG. 11, represent an improvement over conventional systems that merely present the user with suggestions for continuous parameter values. For example, based on FIG. 11, the user does not just get the suggestion "0.15". Rather, the user also sees where the patient lies within the patient population, and whether within the general location of the patient the parameter is very sensitive to the patient characteristic. For example, the user can derive from the graph that a value for Parameter A of 0.15 seems most appropriate, but also that among patients similar to the patient to be treated, there is no great variation in the value of Parameter A. To give even more information, the line graph can also show a confidence interval, e.g. by means of vertical bars (so-called "whiskers") or a shaded area round the value curve.

As another example, the results of a historical-data analysis linking the chance or risk of an intra-operative or post-operative event, observation or outcome to a treatment decision or parameter may also be shown in graphs, area charts or bar charts—optionally with confidence intervals—or in color or patterned plots. In the same way as the location of the patient within a population is displayed in the examples above, the current selection for a decision option or parameter value may be displayed. In some embodiments, the graph, chart or color plot may be displayed together with a depiction of the patient's anatomy and/or any devices, instruments or implants forming part of the planned treatment, such as 2D or 3D images, line drawings, medical images or virtual models. Graphs, charts, color plots and depictions may all be interactive, and changes made in one may be automatically reflected in the other.

Figure 12:
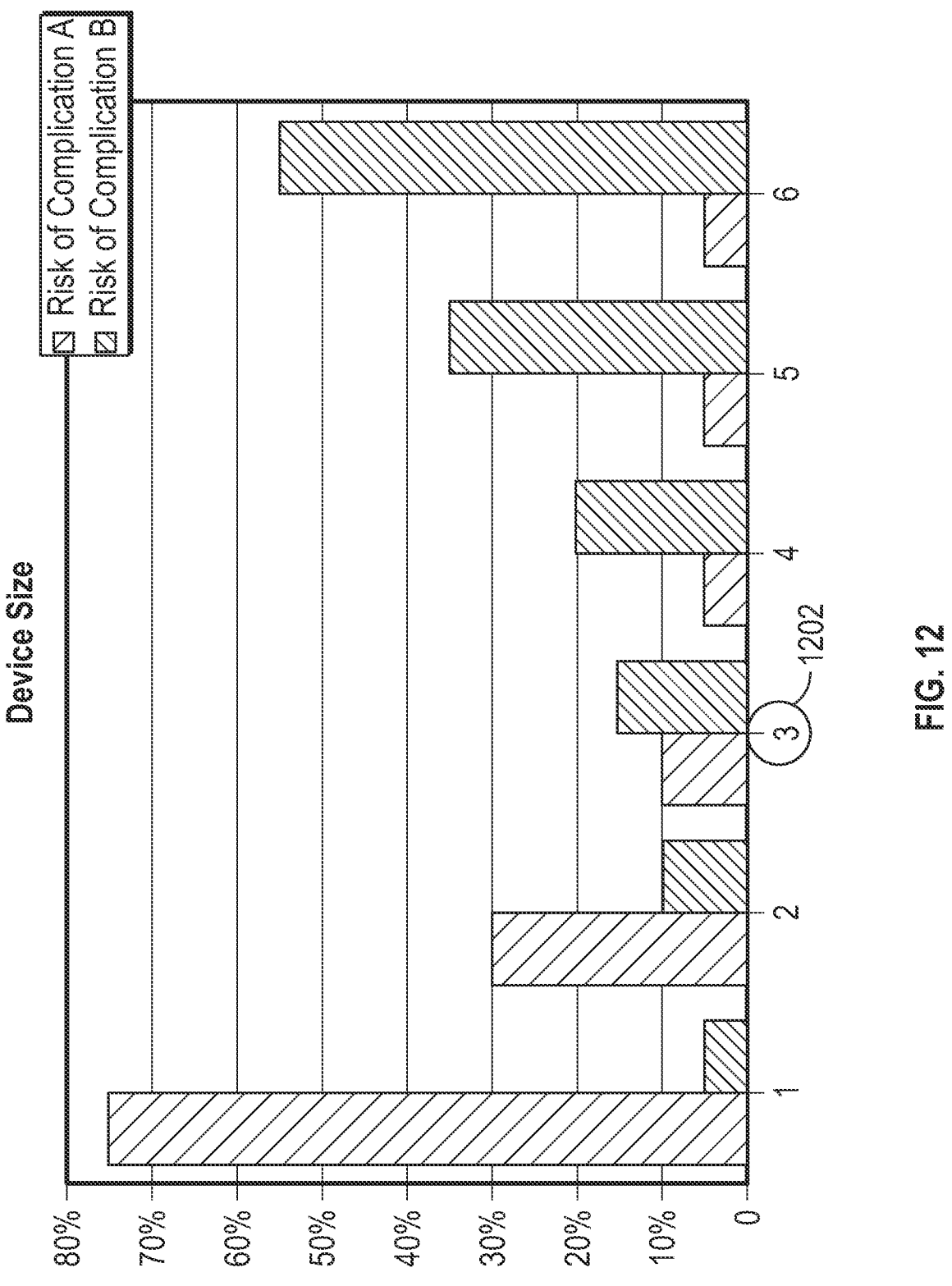
FIG. 12 depicts an example of a historical data-based analysis of patient populations for assessing a device size.

For example, FIG. 12 depicts an example of results of historical-data analysis represented in the form of a bar chart. Here, the risks of two complications are related to a chosen device size. The currently chosen device size is indicated by means of a circle 1202, but other means are possible, such as by means of the opacity, saturation, color, pattern, or the like of the bars in the chart. From this the user may derive that device sizes 3 and 4 seem most appropriate.

Figure 13:
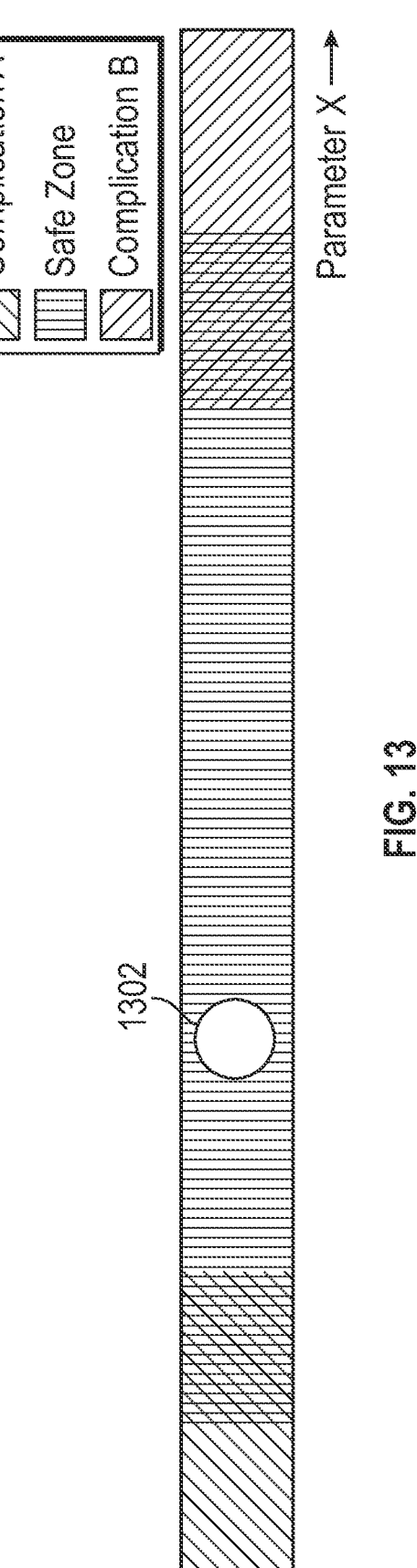
FIG. 13 depicts an example of a historical data-based analysis of patient populations for assessing a parameter value.

FIG. 13 depicts yet another example of results of historical-data analysis represented in the form of a color plot. Here, the risks of two complications are related to a chosen parameter value. The currently chosen parameter value is indicated by the circle 1302. From this the user may derive that the chosen value lies within the safe zone.

The various methods of displaying decision support data in the example figures described herein represent an important improvement over conventional systems that merely present the user with suggestions for decision options or parameter values. For example, from the representations shown in FIGS. 12 and 13, the user does not just get the suggestion "Device size 3" or "Parameter X=x". Rather, the user also sees what the implications are of diverting from the suggestion, how great the chance of an outcome or risk of a complication is, how sharply that chance or risk increases or decreases when changing decision options or parameter values, and therefore how much leeway the user has in varying decision options or parameter values. For example, the user can derive from the plot that the current value for Parameter X is within the safe zone, but also that, whereas it may be safe to increase that value slightly, decreasing it does not seem advisable. One or more such historical-data analysis representations may be displayed to the user at any given instance.

Example Application: Shoulder Treatment Decision Support

Different treatments are available for shoulder-related complaints, depending on the pathology. For example, shoulder arthritis may be treated with rest, medication, corticosteroid injections, arthroscopic debridement, hemiarthroplasty, resection arthroplasty, total (anatomical) shoulder replacement (TSA), reverse shoulder replacement (RSA), and others. Depending on the complexity of the pathology or treatment, some physicians may also choose to refer the patient to a colleague or another hospital or follow the treatment option of one of the known peers.

The systems and methods of the present invention can assist the physician in deciding on a treatment based on patient characteristics and historical data.

For example, based on medical images of the bone and/or cartilage anatomy of the patient, such as CT or MM images, a virtual 3D model of the anatomy of patient's shoulder can be made. The defect can be quantified in the way described above. The result of the quantification may be presented to the user, for example with a depiction as in FIG. 14.

Figure 14:
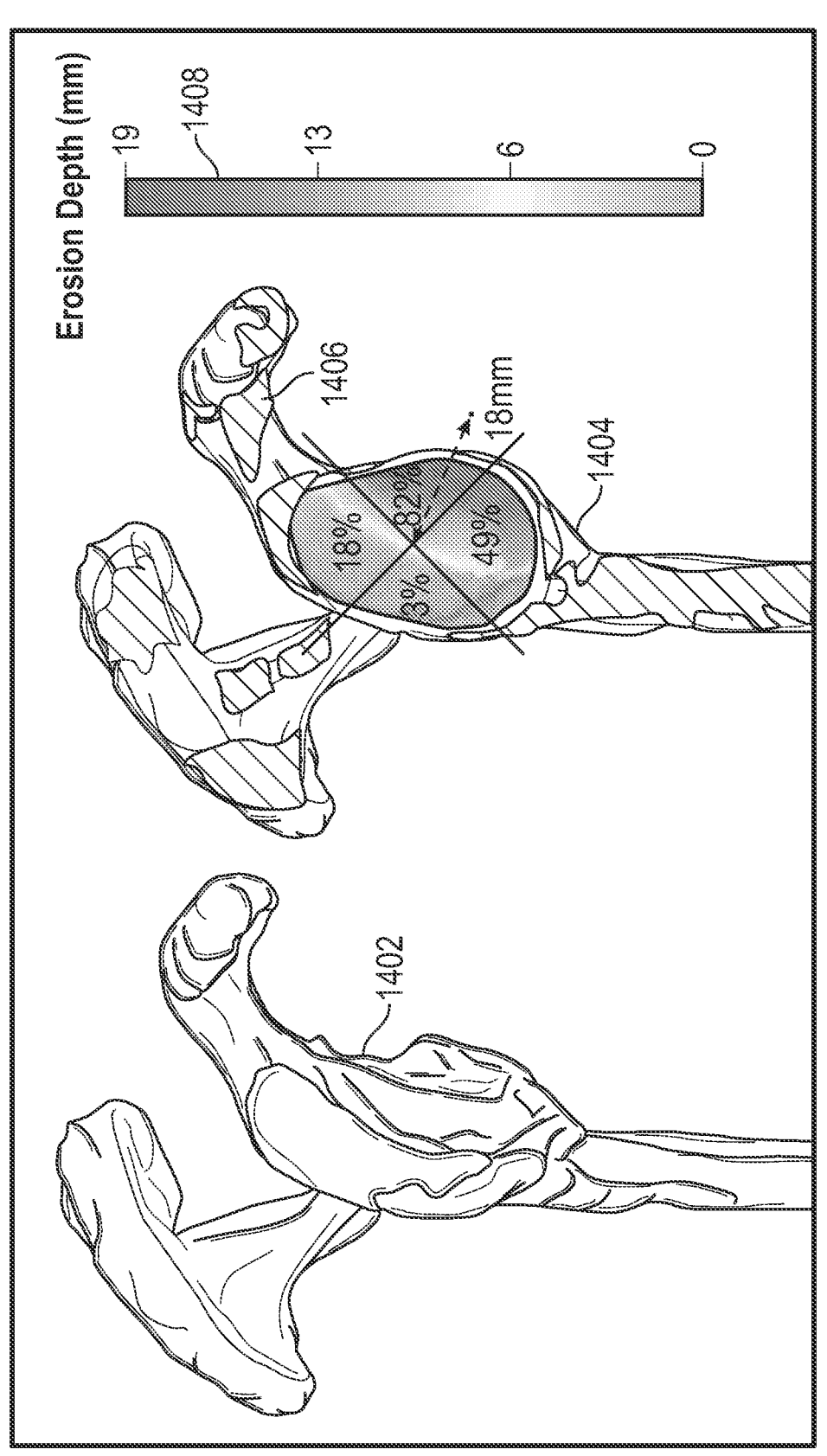
FIG. 14 depicts an example of a defect quantification.

In particular, FIG. 14 depicts an example of a representation of the result of the defect quantification of a glenoid. On the left-hand side, a virtual 3D model 1402 of the bony anatomy of the patient's scapula, with the glenoid in the center. On the right-hand side that anatomy 1404 is shown overlaid onto an SSM 1406 representing healthy anatomy, fit to parts of the patient's scapula. Different results of the defect quantification are shown. The erosion depth (the distance from the actual bone surface to where that surface would have been in a healthy situation, represented here by the surface of the SSM instance) is shown in the form of a gradient plot 1408.

In the example of FIG. 14, erosion depth is computed perpendicular to the best-fit plane through the surface of the glenoid cavity of the SSM instance. Other measuring directions are possible, such as locally perpendicular to the surface of the glenoid cavity of the SSM instance.

Additional measures are computed and shown, such as vault loss percentage (the percentage of the volume of the glenoid vault lost due to bone erosion), erosion area percentage (the percentage of the surface area of the glenoid cavity affected by bone erosion), and the maximum erosion depth. In the example, the glenoid is also subdivided into four quadrants, and a quantitative metric, such as an anterior, posterior, superior or inferior vault loss percentage, is shown in each quadrant. In addition, the subluxation distance is computed. To this end, the center of rotation of the humeral head is computed by best-fitting a sphere to the articular surface of the humeral head; the center point of this sphere is projected perpendicularly onto the best-fit plane through the surface of the glenoid cavity of the SSM instance; the distance between this projected point and the geometric center of the glenoid cavity is measured and displayed. Also, the subluxation region is displayed, i.e. the quadrant in which the humeral head's center of rotation is projected.

FIG. 14 demonstrates an important improvement over conventional systems in that from this information and from the depiction, the user now has reproducible and objective information to assess the extent and location of the bone defect. This information is important for deciding on the most appropriate treatment.

The system may further support a decision by presenting statistical information based on historical data, as described above. For example, systems that comprise a feedback loop for approved pre-operative plans may run an analysis to relate any of the metrics described above to the treatment chosen in previous cases. The result of this historical-data analysis may be presented to the user in any of the ways described above. For example, the results may be presented in a chart, such as in FIG. 15.

Figure 15:
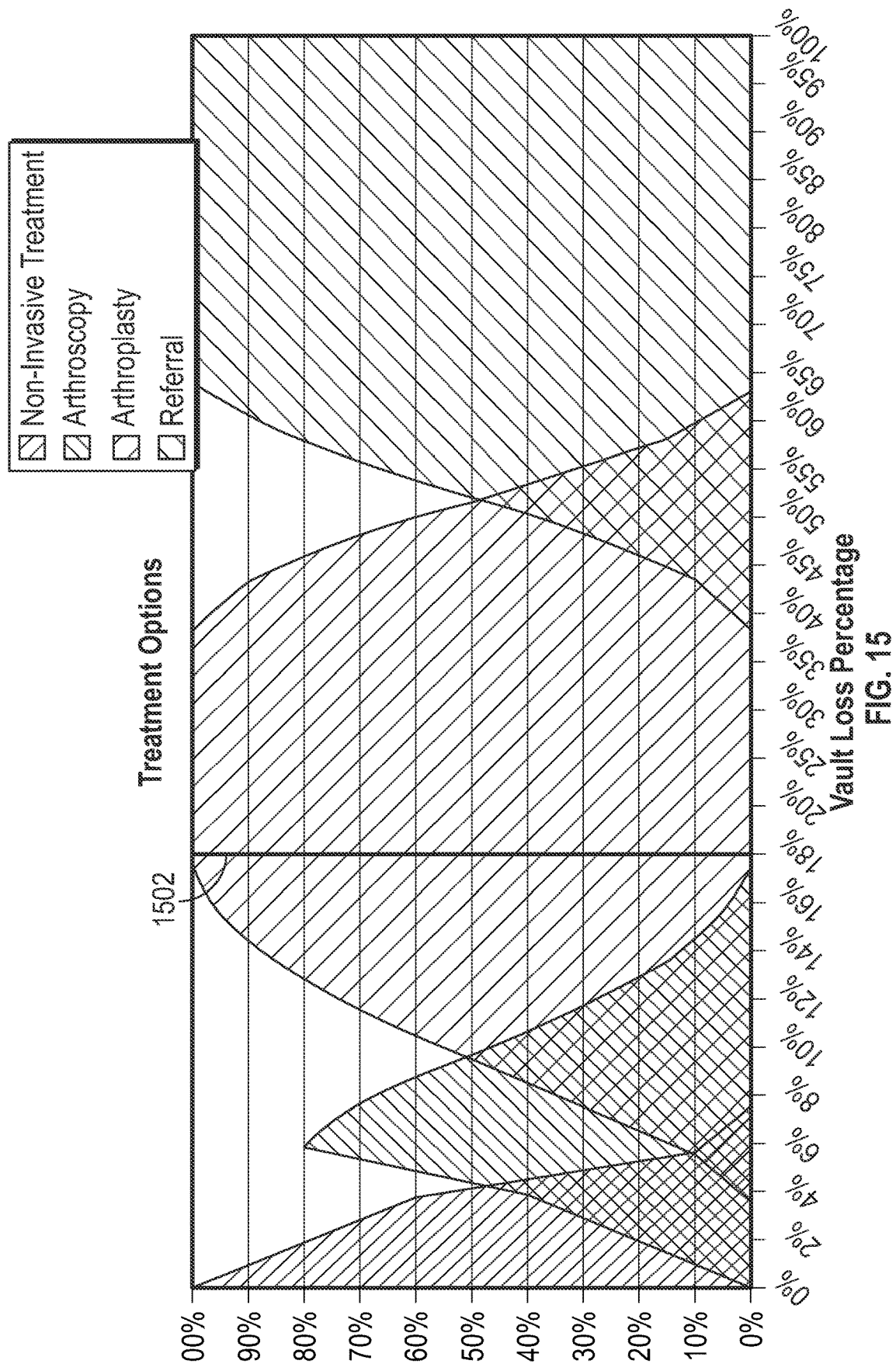
FIG. 15 depicts an example of a historical data-based analysis of patient populations for assessing treatment options.

In particular, FIG. 15 depicts an example of a representation of the results of a historical-data analysis and indicates what percentages of patients have been treated in different ways, sorted according to vault loss percentage. The patient to be treated is indicated with the vertical line 1502.

All records in the database may be used as basis for the historical-data analysis. Alternatively, the population selected as basis for the historical-data analysis may be limited in a number of ways. For example, limiting the population to only those cases that have been treated by the user, the user will get insight as to how the patient to be treated relates to his past experience. Including cases of more or all users will give insight into the practices of a larger surgeon community, such as all surgeons of a particular hospital, country or the world.

The population may also be limited to patients that show a certain similarity to the patient to be treated. Such similarity may be based on one or more patient characteristics, such as sex, age, ethnicity, activity level, and others.

Referral to a colleague or other hospital may be one of the options. Based on the information stored in the database, the system may have the functionality to suggest a clinician who is open to referrals. Based on historical data in the database, the system may even suggest a clinician who has more experience with similar patients, i.e. patients that exhibit similar pathology and/or other patient characteristics or suggest to follow the treatment plan of the referred surgeon.

The historical-data analyses have now been described based on approved pre-op plans gathered and stored through a feedback loop. However, similar and potentially more relevant analyses may be performed on intra-op or post-op data gathered through other feedback loops. Such data may not represent the treatments surgeons intended to give, but the actual treatments administered.

Example Application: Shoulder Surgery Implant Type Decision Support

Similar to the previous example, systems described herein may provide support for the decision of which type of implant to use in shoulder arthroplasty, including, for example, off-the-shelf implant versus custom implant, etc.

For example, the system may offer decision support in the form of historical-data analysis relating the choice between standard or off-the-shelf implants and custom implants to a quantification of the bone defect as described above. The results of the analysis may be presented to the user in the form of a graph, chart, colored or patterned plot, or such as the other examples described herein.

Figure 16:
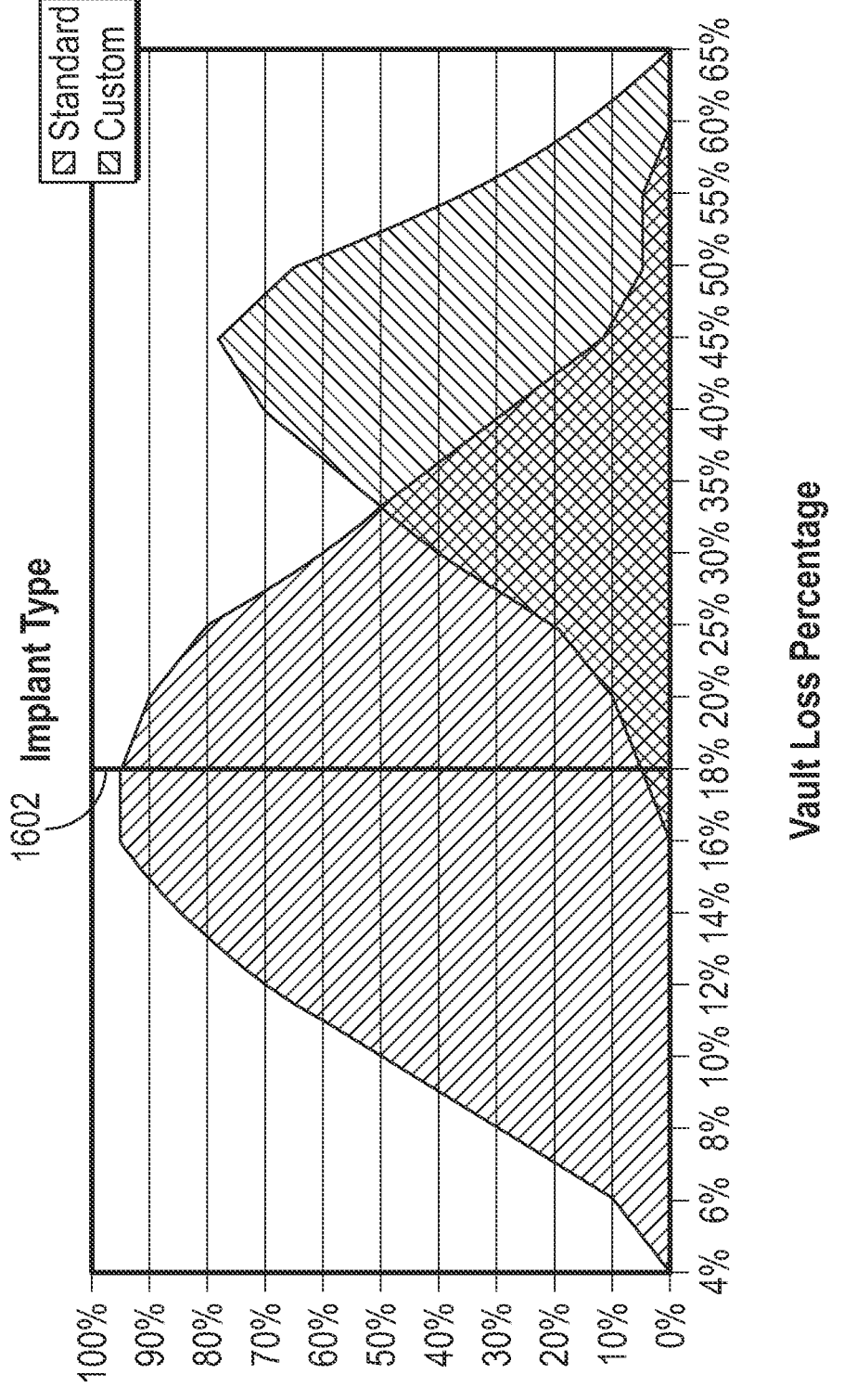
FIG. 16 depicts an example of a historical data-based analysis of patient populations for assessing implant options.

For example, FIG. 16 depicts an example of a representation of the results of a historical-data analysis relating the choice between a standard implant and a custom implant to the vault loss percentage of the patient's glenoid. The patient to be treated is indicated with the vertical line 1602.

Figure 17:
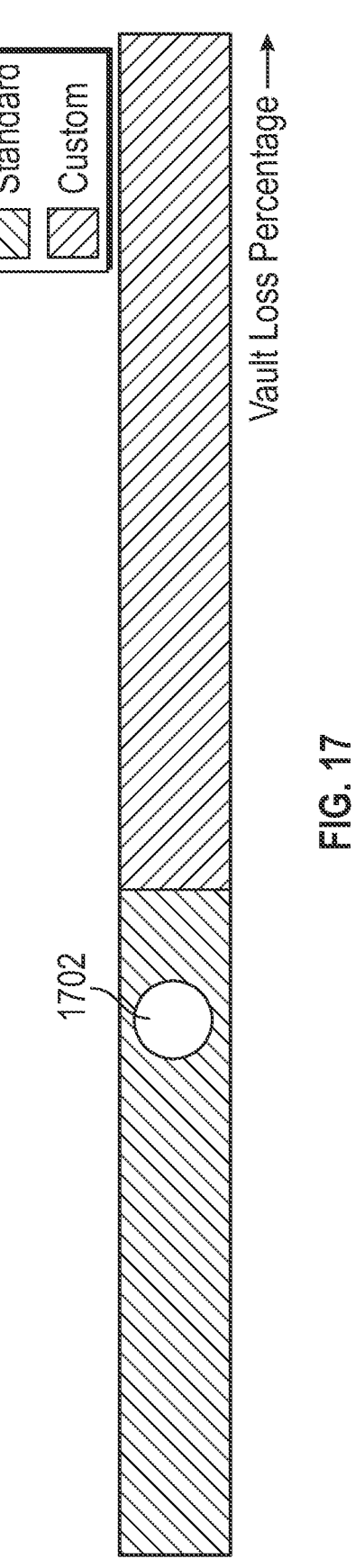
FIG. 17 depicts an example of a historical data-based analysis of patient populations for assessing implant options.

FIG. 17 depicts another example of a representation of the results of a historical-data analysis relating the choice between a standard implant and a custom implant to the vault loss percentage of the patient's glenoid. The patient to be treated is indicated with the circle 1702.

As another example, the system may be provided with a library of implants, and the analysis may relate the choice of implant to one or more defect characteristics as computed from the defect quantification.

Example Application: Shoulder Surgery, RSA Lateralization

In reverse shoulder arthroplasty, lateralization of the center of rotation is often employed as a way to improve the torque generated by the rotator cuff and increase internal and external rotation. However, excessive lateralization can lead to excessive muscle lengthening and even to acromion fracture due to the increased loading. Insufficient lateralization can lead to instability of the joint due to a decrease of the muscle loads.

The systems described herein may therefore offer decision support through simulation of muscle lengthening due to lateralization.

For example, the system may provide a 2D or 3D depiction of the patient's anatomy and the implant. This depiction may comprise virtual models of the bony anatomy of the scapula and humerus, the implant and one or more shoulder muscles. The shoulder muscles may be shown in their actual shape, or rather schematically, e.g. by means of lines, curves, polylines or cylindrical shapes. The depiction may simulate how the muscle trajectories vary with lateralization of the implant and display as a biomechanical model. For reference, the depiction may display the muscle trajectories and bone models in the native—i.e. either pre-operative or healthy—situation in overlay. The pre-operative situation may be derived from the medical images. The healthy situation may be approximated by fitting an SSM representing healthy shoulder anatomy to parts of the patient's anatomy.

Figure 18:
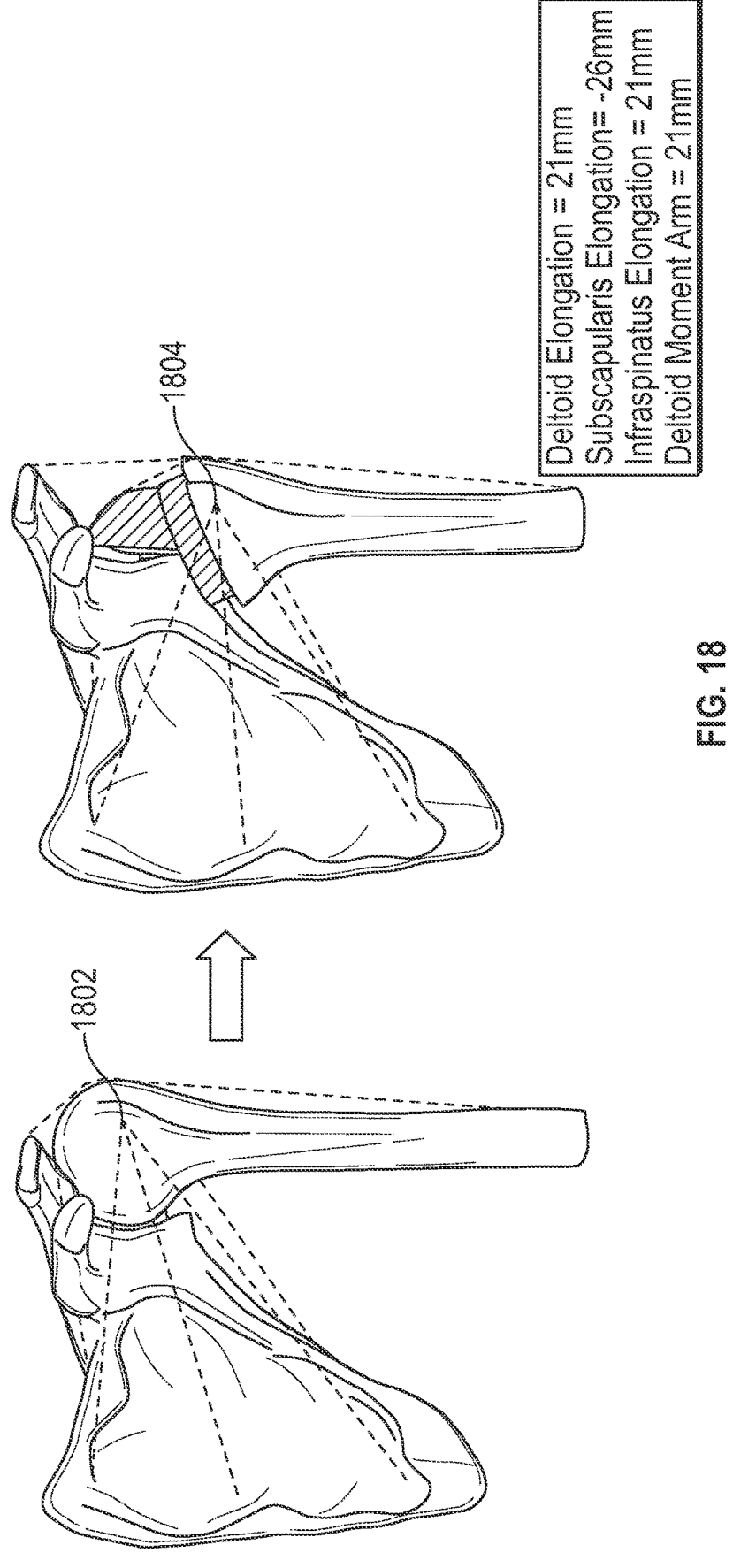
FIG. 18 depicts an example of an interactive surgical planning system.

The system may be interactive. For example, as shown in FIG. 18, the system may allow the user to manually shift the center of rotation from a first position 1802 to a second position 1804 by, for example, manipulating the model of the implant by clicking and dragging an input device, such as a computer mouse. Alternatively, the system may provide user interface controls, such as buttons or sliders, to adjust the lateralization. The depiction is automatically updated to reflect the adjustments made. For example, the relative positions of the scapula, humerus and implant components and the corresponding muscle trajectories are updated.

The system may display numerical values, such as percentages, quantifying the amount of lengthening of individual muscles, or in terms of decreasing thickness of the lines, curves, polylines, or cylindrical shapes, or an average for some or all muscles. These values may be overlaid onto the depiction of the anatomy, or listed elsewhere in the user interface.

The systems according to the invention may provide additional decision support through historical-data analysis of past cases. As before, the data for such an analysis may be gathered through one or more feedback loops in the form of approved pre-operative plans or actually executed operative plans gathered intra-operative or post-operative. The population may be based on all available records, or may be limited in different ways as described above. In preferred embodiments, the population is limited to patients who show a certain similarity to the patient to be treated in one or more patient characteristics. For example, bone density may be derived from CT scans and may play an important role in assessing the risk of acromion fractures. Alternatively or additionally, shape characteristics, such as the thickness of the acromion, may play an important role. Those shape characteristics may be quantified by means of certain measurements or by means of parameter values of an SSM fit to the anatomy of the patient, as described above. The results of the analysis may be displayed in the form of graphs, charts or color plots displaying for different amounts of lateralization how often those amounts have been planned or implemented before. The current lateralization may be indicated on the graph, chart or color plot by means of a marker, such as a line, dot, diamond or the like.

Alternatively, the analysis may investigate how often an amount of muscle lengthening was planned or implemented before. This could be an amount of muscle lengthening of an individual muscle, and average of a selection of or all shoulder muscles, or a weighted average of a selection of or all shoulder muscles.

Finally, in embodiments where the system gathers and stores information regarding intra-op or post-op complications, the analysis may additionally include the risk of such complications, such as acromion fracture or instability. The user may then see, from the graph, chart or color plot, not only whether the chosen lateralization falls within common practice, but also within the safe zone.

In addition or alternative to the interactive features described above, the graph, chart or color plot may be interactive. For example, the user may choose an amount of lateralization by clicking on the graph, chart or color plot, or by sliding the marker representing the current amount of lateralization. Any depiction of the anatomy and planned implant(s) may be automatically updated to reflect the change in lateralization.

The systems and methods described herein can be operated and performed by, for example, computing devices, such as desktop computers, portable computers, portable electronic devices, tablet computers, smart phones, and other computerized devices. In some implementations, the methods described herein may be performed by native software applications while in others they may be performed in server-client implementations. For example, in some implementations, software configured to perform the methods described herein may be hosted by a remote server or a cloud-based system. In some cases, various aspects of the systems and methods described herein may be distributed across different computing devices.

Further, the systems and methods described herein can be operated and performed by, for example a medical professional, such as a surgeon, doctor, or nurse, or by a non-medical professional, such as a clinical technician, design engineer, implant manufacturer (e.g., to give him an overview of what kind of implants a particular surgeon works with and generate a plot depicting the same to him), a residency student, or a patient (e.g., who is walked through the surgery before the actual surgery).

Example Application: CMF Treatment Decision Support

The defect quantification system described herein may further be used to detect one or more of defects in the craniomaxillofacial (CMF) region and further classify it, such as trauma; orbital reconstruction; distraction osteogenesis; temporomandibular joint; cranial vault reconstruction; congenital craniofacial deformities, such as craniosynostosis; dental alveolar surgery; or any other cosmetic or reconstruction surgeries comprising of one or more of the parts of the craniomaxillofacial regions.

As an example embodiment, the defect quantification system described herein may use patient data (e.g., imaging data) and one or more feedback loops to detect the type of defect to be quantified and then to classify the defect such as orthognathic defect.

In one example of a method, one or more medical images or scans (generally, imaging data) of a patient's anatomy requiring correction may be acquired. For example, the imaging data may relate to a jaw deformity of the patient. In this example, the imaging data may include, for example, image data of one or more of a mandible, maxilla, or chin of the patient. As described above, the anatomy in the imaging data may be segmented (e.g., between mandible, maxilla, and/or chin) to obtain a virtual three-dimensional surface model. Then, a statistical shape model of a healthy anatomy (e.g., a healthy jaw) may be fitted to the three-dimensional surface model to identify healthy and damaged portions of the patient's anatomy (e.g., a damaged portion of the patient's jaw).

Figure 19:
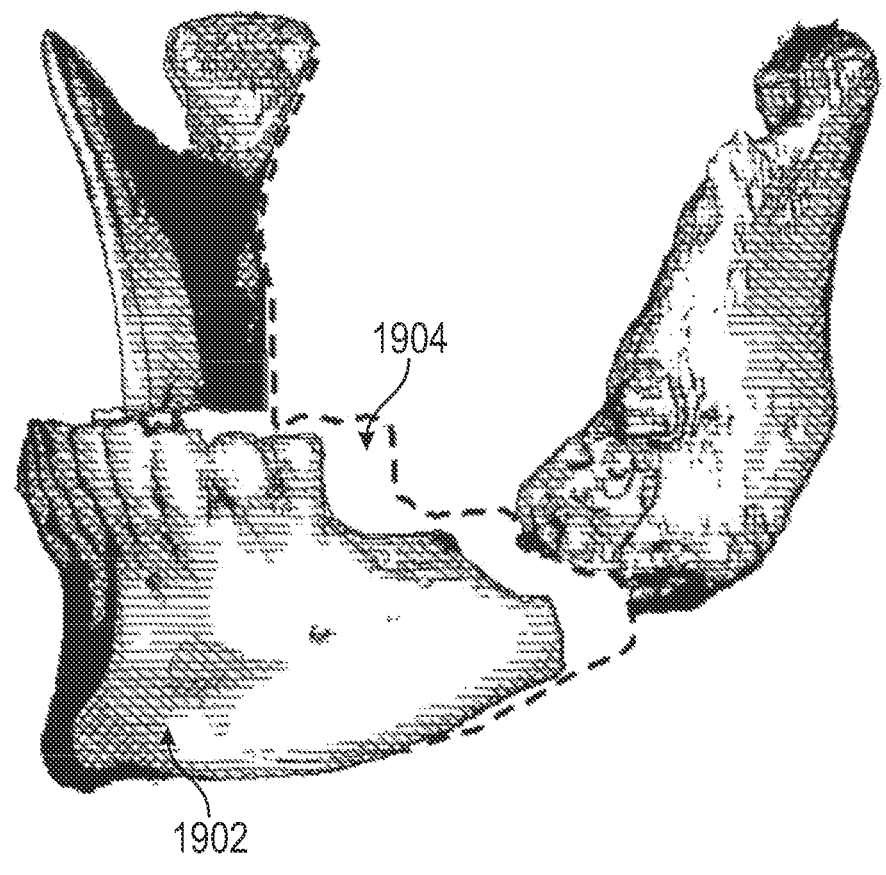
FIG. 19 depicts an example of a representation of a defect quantification using patient imaging data and an SSM.

FIG. 19 depicts an example of a representation of a defect quantification using patient imaging data and an SSM. In this example, the imaging data comprises a three-dimensional model of the patient's bony mandible anatomy 1902 overlaid on an SSM 1904 of an original, healthy mandible.

It is evident in this example that this patient only requires treatment of the mandible and not the maxilla.

The manner of comparing the patient's actual anatomy (e.g., by way of three-dimensional models created from medical imaging data) to a healthy anatomy model (e.g., an SSM model) allows a surgeon to visualise the possible surgical approaches. For example, in this case, the surgeon can manipulate the positioning of the mandible while providing the healthy anatomy as reference. In this example, the defect shown in FIG. 19 and a proposed surgical treatment may be identified, such as mandible reconstruction.

Figure 20:
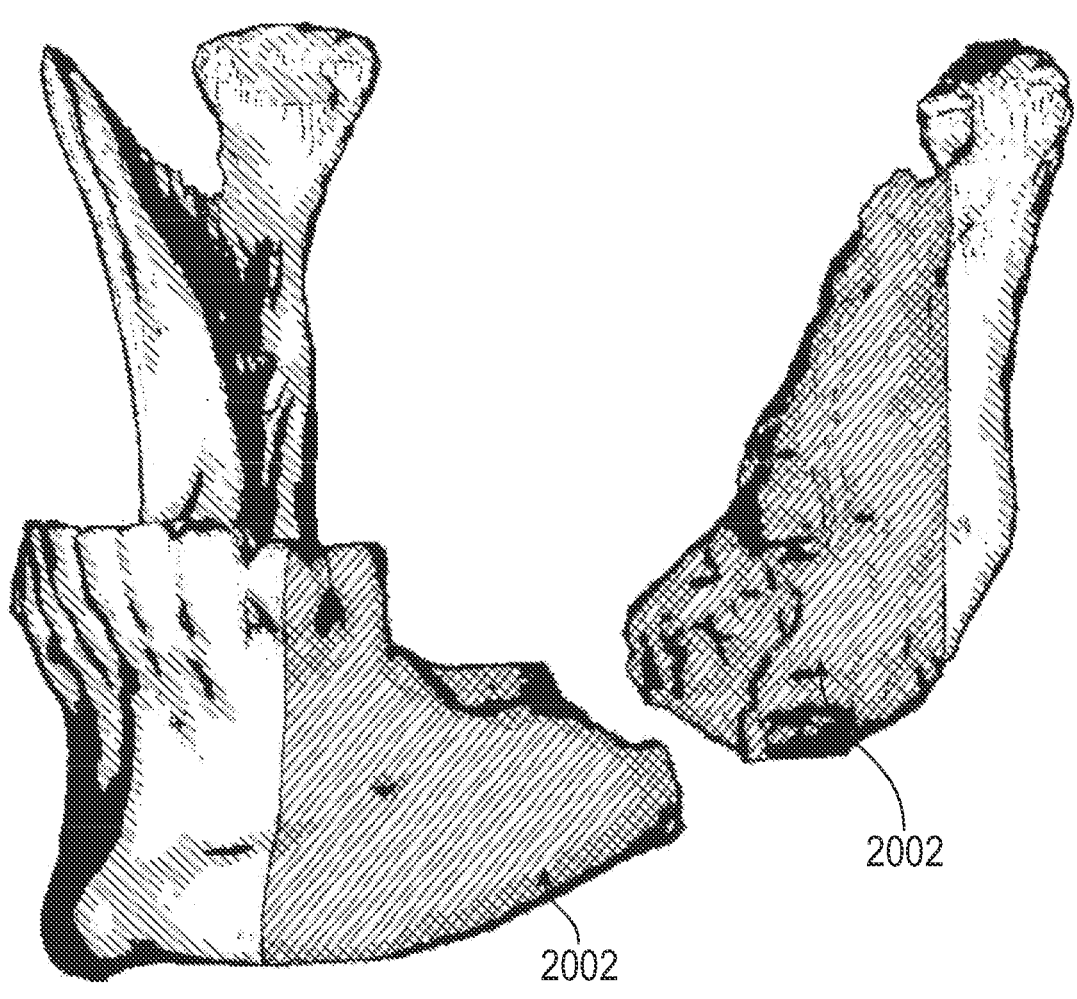
FIG. 20 depicts an example representation of a treatment option in a three-dimensional patient anatomy model.

During the planning stage, the system guides the surgeon by showing portions of the anatomy that may be resected 2002, as depicted in FIG. 20. In particular, the system shows clear resection margins and may warn the surgeon if he decides to resect more or less bone than is necessary based on the quantified defect.

Further, as described above, the three-dimensional patient anatomy model may be accompanied by historical data associated with the patient and may suggest a patient-specific implant for the planned treatment. For example, the treatment plan may include the use of bone graft, and, based on patient's history, the patient's left fibula may be chosen for the graft. The system may further indicate the healthy parts on the fibula and show post-op result. Notably, these are just a few examples.

In another example, a proposed treatment plan may involve treatment of the additional CMF regions, including the maxilla, mandible, and genioplasty.

Figure 21A:
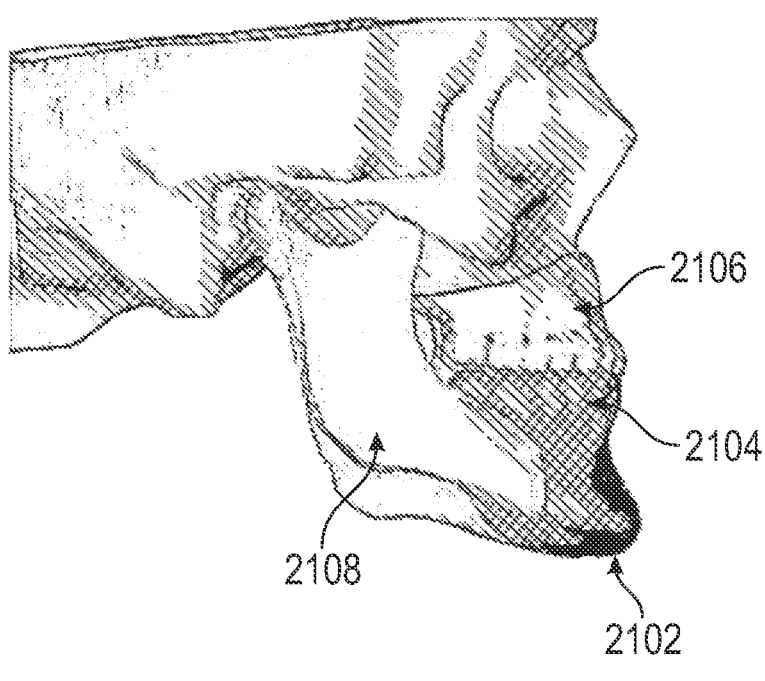
FIGS. 21A-D depict example representations of a treatment option in a three-dimensional patient anatomy model.

FIG. 21A depict an example in which a defect is classified as LeFort I, which is a type of fracture of the skull involving the maxillary bone and surrounding structures in either a horizontal, pyramidal or transverse direction. For such a classification, the treatment plan may involve bilateral sagittal split osteotomy (BSSO) and genioplasty osteotomy. As above, a model of the patient's anatomy is segmented into various regions 2102-2108, which may be used for the defect quantification and considered during pre-op planning.

Figure 21B:
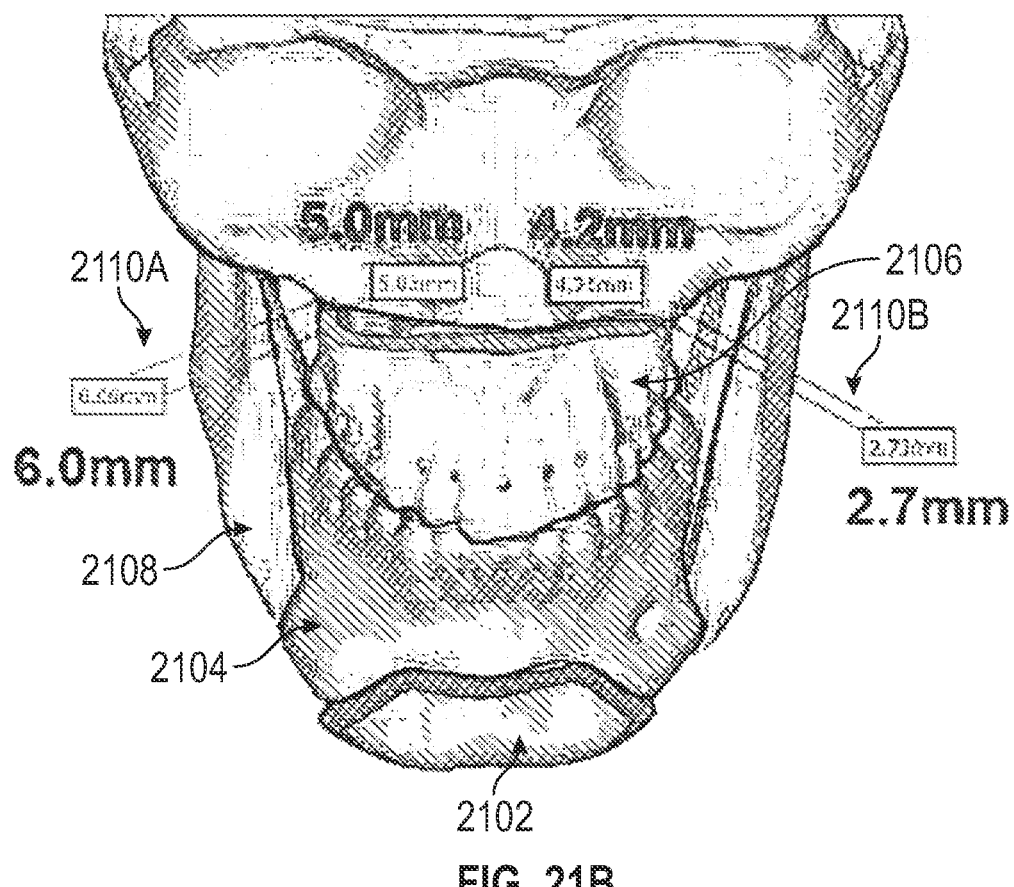

FIG. 21B depicts aspects of the treatment of the defect quantified in FIG. 21A. In particular, FIG. 21B depicts a recommended distance of maxillary movement to treat the defect. In some cases, the recommended distance may be based on historical data and the system may further show ranges 2110A and 2110B (e.g., in mm) of maxillary movement possible.

Figure 21C:
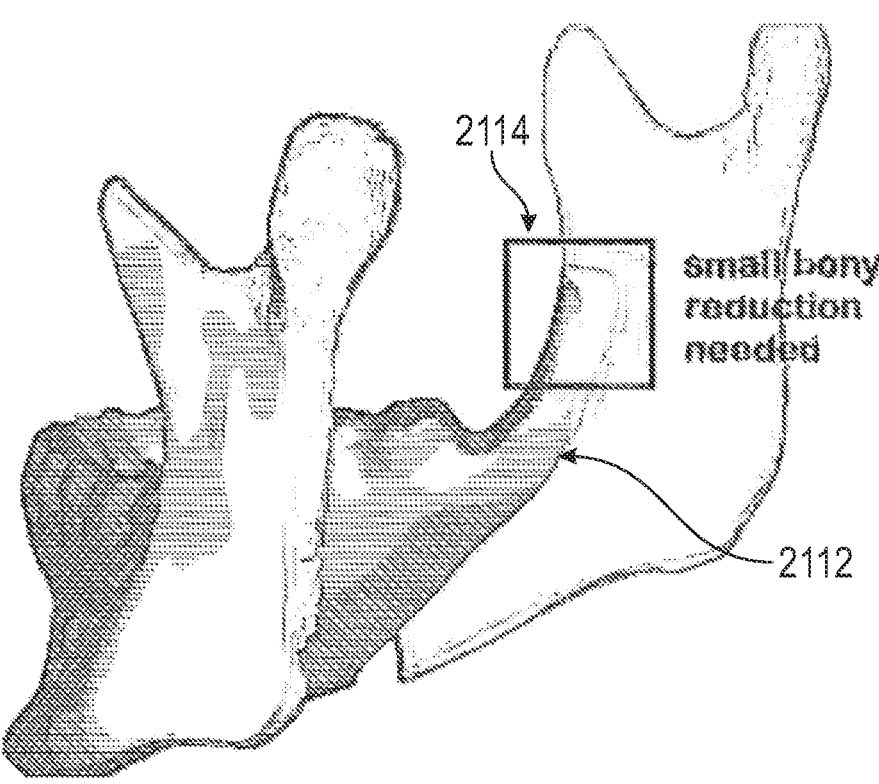

FIG. 21C depicts an example of proximal overlap and a resection margin 2112. In particular, FIG. 21C identifies at 2114 that a reduction of the bony anatomy is necessary.

Figure 21D:
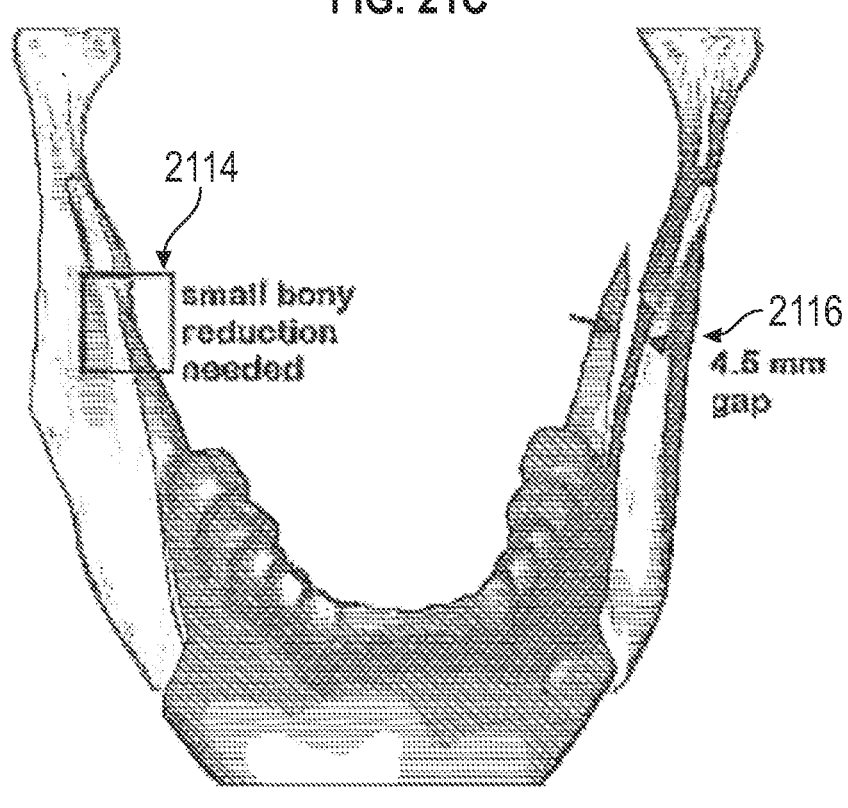

FIG. 21D depicts another example of the proposed treatment of the defect. In this example, the system displays a warning 2116 that a gap needs to be filled.

In some embodiments, based on the quantified defect and initial treatment plan, the system may further suggest relevant implant types and sizes to connect the different bone parts, such as to fill the identified gap in FIG. 21D. For example, the system may suggest use of a guide for placement of the mandible implants. The system may further allow a surgeon to visualise different implant options before making a choice and updating the treatment plan accordingly.

Example Application: Orthognathic Surgery Decision Support

Another example application of the surgical planning systems described herein is orthognathic surgery decision support. In one example, a pre-operative planning tool (e.g., Proplan CMF by MATERIALISE®, and others) may be used to generate a pre-operative surgical plan for a specific craniomaxillofacial surgery. Imaging data from the pre-operating planning tools may then be used by a defect quantification system, such as described herein.

In one example, a defect may be classified as a jaw deformity requiring orthognathic surgery to remedy the defect. In this example, the defect quantification system may quantify the defect based on the various existing osteotomy classifications familiar to surgeons, such as Limberg's oblique subcondylar osteotomy, Moose's procedures for mandibular reduction, Caldwell and Letterman's vertical ramus osteotomy, Trauner and Obwesefer's sagittal split osteotomy (SSO), bilateral sagittal split osteotomy (BSSO), Winstanley's intraoral vertical ramus osteotomy (IVRO), and others. The defect quantification system may further allow the user to visualise different fractures of the skull, such as Lefort I, Lefort II, modified LeFort I, and others, if the defect is in the maxilla.

Alternatively or additionally, the defect quantification system may classify the defect based on a type of incision or surgery as well. For example, based on the defect and the SSM model generated, a user may choose to perform a bi-max (maxilla+mandible), multi-segment maxilla, maxilla only, mandible only, or genioplasty surgery.

Once the defect has been quantified, a default treatment plan may be created as described above. In some cases, three-dimensional cephalometry data (measuring deviation from the norm), asymmetry assessments, and records of previous surgeries, as well as other types of patient data stored with a patient profile, may be considered.

In one example, if the defect is in the mandible, a bilateral sagittal split osteotomy (BSSO) may be proposed by the surgical planning system. In some cases, this treatment may be performed without any treatment of the upper (maxilla) jaw. The surgical planning system may allow a user (e.g., a surgeon or other medical practitioner) to visualise the mandible surgical approaches with appropriate changes in the maxilla and allow the user to decide the best approach.

In some embodiments, the system may further assist the surgeon in selecting the exact type of BSSO to select, such as Dalpont, Obwegeser, short ramus osteotomy, inverted L, and vertical ramus. Depending upon the defect and the type of osteotomy, the system may provide warnings such as proximity or damage to surrounding nerves and propose a suitable osteotomy. The surgical planning system may further warn the user when too much bone or too little bone has been resected in the planned treatment. The surgical planning system may further prompt the user with appropriate resection margins and warn when margins are exceeded in comparison to the historical data of a selected patient population (e.g., a population in which the patient for which the surgery is being planned is a part).

Based on the type of osteotomy, the surgical planning system may further help the user decide on a suitable fixation method, such as patient-specific or standard, and the area upon which the fixation method would be placed. Some of the options available to the user may include selection of one or more plates, type of plates (patient-specific or standard plates), use of guides, and/or use of lag screws, etc.

In some embodiments, if the treatment plan involves treatment of the maxilla, the user may choose between two or more plates based on the patient history and may be able to compare the type and choice of number of plates chosen for similar patients using historical data analysis and/or patient population plots.

In some embodiments, if the treatment plan involves treatment of the mandible, the surgical planning system may allow the user to visualise plate or lag screw positioning and orientation, superior or inferior fixation areas, etc. The surgical planning system may further allow the selection of thickness and width of the plates, fixation material based on amount of bone available (e.g., CPTi, TAIV, bioresorbable), number and location of fixation screws on each side of osteotomy, use of guides in combination with patient-specific or standard plates, and others. All of the aforementioned selections and configurations may become part of the treatment plan generated by the surgical planning system.

In an example embodiment, the defect quantification system may classify a patient as having a class 2, narrow maxilla defect requiring treatment of the mandibular advancement and maxillary impaction. The default treatment plan may include treatment of the maxilla, such as multi-segment Lefort I osteotomy and BSSO for the mandible. The default treatment plan may further recommend use of a patient specific plate for the maxilla and three lag screws on each side for the mandible. The user (e.g., a surgeon) of the surgical planning system may approve the default treatment plan or may explore modifications to the plan through the surgical planning system's ability to visualize the treatment plan.

The user may then approve the treatment plan and use it in during the surgery (e.g., in the operating room). While in the operating room, changes or deviations from the treatment plan may be entered into the surgical planning system, such as time required to perform a surgical step, anastomosis, ischemic time for bone graft harvesting, required surgical equipment check before the start of the surgery, blood loss, timed checks on pathologic tissues to determine accurate resection margins, and others.

After the surgery is complete, the patient's profile may be updated and certain data regarding the treatment may be generated for future pre-operating surgical planning as well as for historical data analysis, which may be used as described above. Other post-operation data may likewise be included in the patient profile, such as infection rate, stability and relapse rate, pain score, hospital discharge and related notes, mouth openings scans and notes, recurrence and relapse rate for oncology cases, flap survival rate for reconstructive surgeries, functional outcomes, and aesthetic outcomes, among others.

Example Application: Reconstructive Surgery Decision Support

Another example application of the surgical planning systems described herein is reconstructive surgery decision support. In one example, a pre-operative planning tool (e.g., Proplan CMF by MATERIALISE®, and others) may be used to generate a pre-operative surgical plan for a specific craniomaxillofacial surgery. Imaging data from the pre-operating planning tools may then be used by a defect quantification system, such as described herein.

In one example, a defect may be classified as a deformity involving the mandible or the midface involving reconstructive surgery. Based on patient profile data, such as patient history and patient imaging data, a three-dimensional SSM model may be generated of the patient. The imaging data (showing the defect) and the SSM may then be compared to generate the defect classification. Based on the defect classification, a default treatment plan may be generated by a surgical planning system, such as described herein.

In the case of cancer patients, the defect quantification system may quantify the defect based on the type of cancer and/or lesion (benign or malignant), area of lesion to be excised and treated during the surgery, number of surgeries required, and other factors. Any other patient information, such as other treatments, like chemotherapy, radiation therapy, etc., are also included in the patient profile.

In the case of corrective surgery, the patient history may be taken into account during treatment planning. For example, based on patient imaging data, a user (e.g., a surgeon) can make an assessment of an asymmetry and its deviation from the normal, original anatomy. Using the three-dimensional models based on the patient data, the defect is simulated in comparison with healthy anatomy.

In the case of trauma, the visualisation function of the surgical planning system may be used along with patient population and historical data analysis, in order to create an appropriate treatment plan efficiently. In some embodiments, the surgical planning system may recommend a default plan based on characteristics identified in the trauma patient.

Further, the historical data analysis performed by the surgical planning system may allow the user to compare the success rate of various surgical approaches for a specific indication, such as vascularized graft versus a bone non-vascularised graft, autologous versus bone substitute, and the like.

In some embodiments, the system may also store relevant information required for matching a donor with a recipient, and the surgical planning system may further provide information about other users (e.g., other surgeons) to be contacted or other facilities to contact (e.g., other hospitals) with potential donors. In case tissue has been harvested, the surgical planning system may display the information about donor site morbidity in the case of, for example, a harvested bone graft. In the case of trauma involving larger bone defects, the surgical planning system may prompt the user to use larger, stronger plate and in some cases even patient-specific plates. Notable, these are just some examples and others are possible.

Example Application: Cardiac Treatment

Another example application of the surgical planning systems described herein is cardiac treatment. In one example, a pre-operative planning tool (e.g., MIMICS and MIMICS Enlight by MATERIALISE®) may be used to generate a pre-operative surgical plan for structural heart and other vascular interventions. Imaging data from the pre-operating planning tools may then be used by a defect quantification system, such as described herein.

For example, patient data, including images, scans, patient history, and the like, is stored by the surgical planning system. As described above, the imaging data may be converted into three-dimensional models of a patient's anatomy. An SSM model may then be used by the defect quantification system to classify a heart defect based on congenital or acquired diseases. In some examples, the defect may be classified into septal defects, valvular heart disease, such as of the aorta or mitral valve, vascular obstructions, fistulas and, other conditions. Each category may be further divided into classes based on severity. Once the defect has been quantified, a default treatment plan may be generated, such as described above.

In one example, a patient may be identified with a defect in the aortic valve, indicating a transcatheter aortic valve replacement (TAVR) procedure. Several factors can be determined from the three-dimensional anatomy models and SSM models as part of the defect classification system, which help a user (e.g., a surgeon) in generating a treatment plan, such as aortic valve morphology, assessment of the aortic root, assessment of the annulus (size and height), LVOT calcification, height of the sinutubular junction, assessment of the coronary ostium (height), assessment of the sinus of vulsava (diameter and height), assessment of the risk of coronary artery obstruction, prediction of optimal fluoroscopic projection angles for device deployment, assessment of the transfemoral access route for TAVR device, assessment of alternative routes if transfemoral is not feasible, assessment for carotid protection device feasibility, and others. These factors may impact treatment plan decisions, such as catheter planning, device selection, access planning in case the traditional transfemoral route is not accessible, size of the incision, type of device, and others.

In one example, a patient may be identified with a defect in the mitral valve indicating a transcatheter mitral valve replacement (TMVR) procedure. Several factors can be determined from the three-dimensional anatomy models and SSM models as part of the defect classification system, which help the surgeon in generating a treatment plan, such as assessment of the landing zone involving assessment of mitral annulus size (diameter, height, APML, leaflets), calcification, evaluation for risk of left ventricular outflow tract (LVOT) obstruction, assessment of risk of interaction with other intercardiac devices (new or recently implanted or to be implanted), distance from such devices, determination of optimal trans-septal puncture location or transapical route, assessment of optimal fluoroscopic angles, height of the papillary muscle, volume and size of the left ventricle, assessment of the delivery device and route, angulation of the mitral valve, access location, extend of trans-septal crossing (e.g., fossa ovalis), and others. These factors may impact, for example, the entry points, incision size, type and size of a surgical device, etc. For example, the user (e.g., a surgeon) may determine the entry point such that the apex/ apical puncture is perpendicular to the mitral annulus for the placement of the device. Using the defect quantification system along with historical data, the surgeon may be able to predict the outcome of neoLVOT procedure by using one or more visualisation methods to place the patient in the selected patient population.

In one example, a patient may be identified with a defect in the left atrial appendage (LAA) indicating closure of the LAA. Several factors can be determined from the three-dimensional anatomy models and SSM models as part of the defect classification system, which help the surgeon in generating a treatment plan, such as assessment of the landing zone for device placement, determination of the optimal trans-septal puncture location, determination and assessment of optimal fluoroscopic projection angles for device delivery, selection and planning of the delivery device, selection of the catheter, and angulation to LAA. Based on diameter, height, depth and shape of the LAA, appropriate device and its size may be selected for the treatment plan.

Using historical data and patient population, the surgical planning system may prompt the user with the type and size of device, catheter selection, and route of delivery as few examples. Based on severity of the disease, age of the patient, health risk involved, and availability and viability of the device, the surgical planning system may prompt the user with alternative treatments. For example, open heart surgeries may be considered last. Based on historical data, the system may also store relevant information about catheter delivery and pathways used such as catheter deformation percentages and warn the user to consider a more suitable catheter if one is available.

Other structural heart interventions such as paravalvular leak, atrial septal defect (ASD), patent foramen ovale (PFO) may also be planned using the surgical planning system as described herein.

Further, intra-operative measurements, such as best viewing angles for fluoroscopy or C-arm angles to position the patient correctly during surgery, may also be suggested, and appropriate warnings may be provided both during preoperative planning and via one or more navigation system during the planned treatment (e.g., surgery).

For example, based on imaging data of the anatomy of the patient (e.g., CT or MRI images), a virtual three-dimensional model of the anatomy of a patient's heart can be made. The defect can be quantified in the manners described above.

Figure 22:
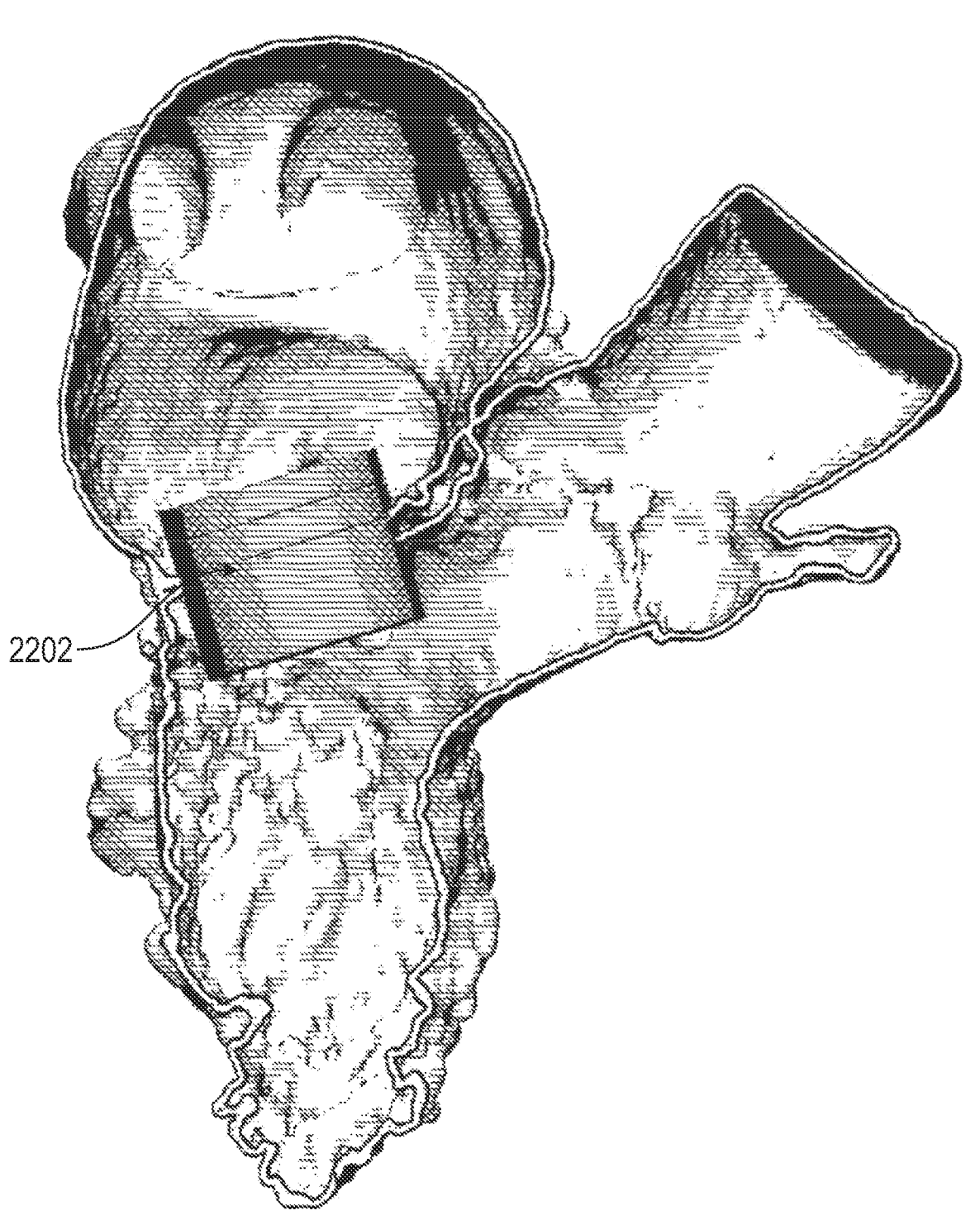
FIG. 22 depicts another example representation of a treatment option in a three-dimensional patient anatomy model.

In the example depicted in FIG. 22, the patient is identified with a defect in the mitral valve.

Structural heart interventions, such as TMVR, involve placement of a mitral valve device 2202, as depicted in FIG. 22. Based on a three-dimensional model of the patient's heart, as depicted in FIG. 22, a user (e.g., surgeon) may determine a size, type, position, and location of an implant. Patient metrics such as angulation, available cross-sectional area corresponding to fluid passageway, and others may be considered. Further, using one or more visualisation tools of the surgical planning system, the risk of leakage may be determined while considering the type of implant. Further yet, a delivery method and access point may also influence the choice of the implant.

In another example, current delivery route for the implant to be delivered may need to be determined for a patient requiring an LAA procedure. In such a case, selection of a catheter based on the patient's anatomy and along with its entry point and delivery trajectory needs to be planned such that during the surgery, the implant is delivered safely to the patient.

Figure 23:
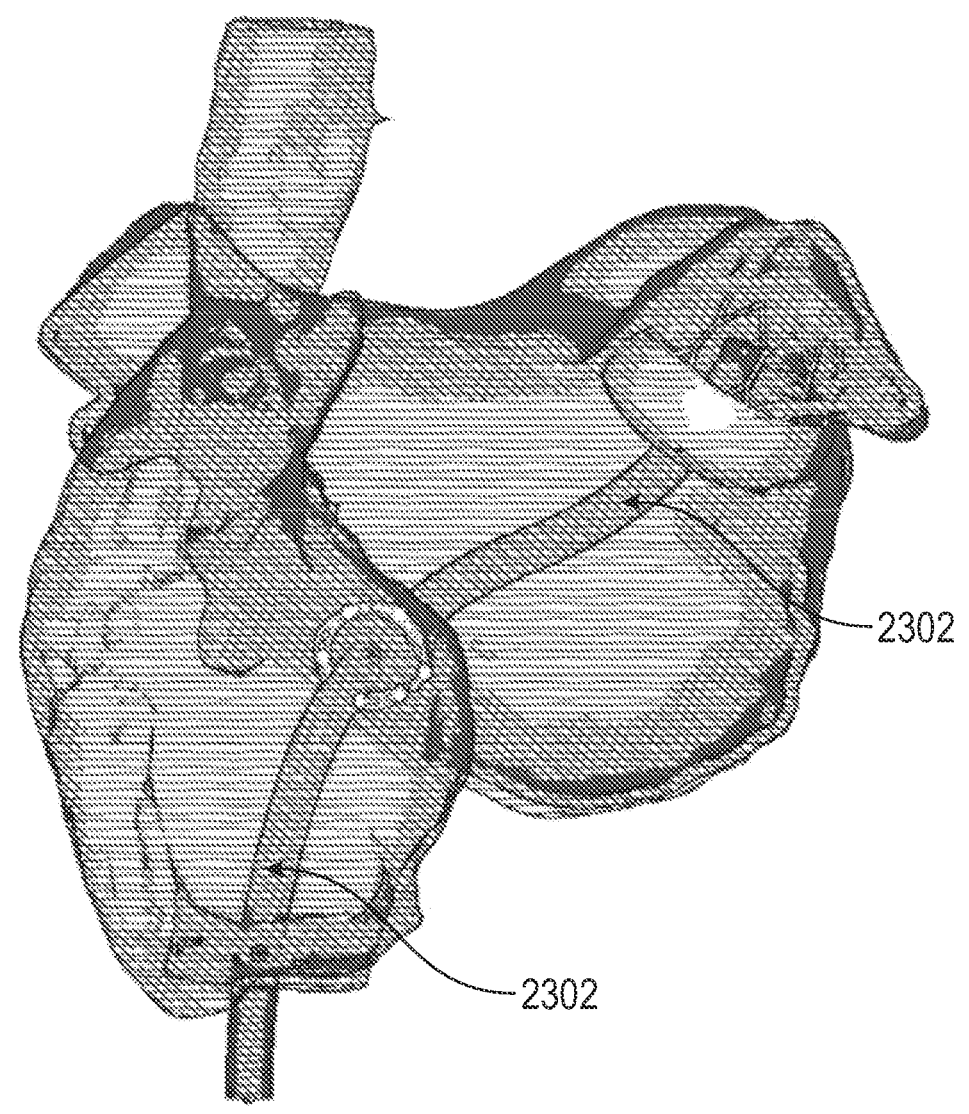
FIG. 23 depicts another example representation of a treatment option in a three-dimensional patient anatomy model.

FIG. 23 depicts a target trajectory 2302 for delivery of an implant. A user of the surgical planning system may experiment with different catheters before making the final treatment plan. Further, if the delivery path selected for the patient would lead to further complications, the surgical planning system may warn the user to reconsider the delivery path.

Example Application: Knee Treatment Decision Support

Another example application of the surgical planning systems described herein is for joint defects (e.g., ankle, hip), such as knee treatment decision support. In one example, a pre-operative planning tool (e.g., SurgiCase Knee Planner by MATERIALISE®), may be used to generate a pre-operative surgical plan for a joint arthroplasty, such as the knee. Patient data, including medical imaging data (e.g., MRI and CT scans), patient history, PROM score before the surgery, new or revision surgery information, patella height, axis, deformity type, and others may be utilized by the surgical planning system to generate a treatment plan.

For example, the defect quantification system may be used to classify the severity of a defect as requiring a total or partial knee arthroplasty. As above, the defect quantification system may compare a three-dimensional model of the patient's anatomy to an SSM model to help quantify the defect. Before or during planning, information such as the type (standard or patient-specific) and size of implant, along with information about the varus/valgus angle, cartilage wear and other soft tissue data, may be presented to the user such that a pre-operative plan may be determined.

In some cases, the user may compare the generated default pre-operative plan with selected patient population and use historical data analysis, as described above. In particular, the surgical planning system may present to the user information about why a certain type of implant was suggested, the position and location of the implant, the varus/valgus angle to be considered, and the system may enable the user to visualise how changing the implant characteristics affects the patient's expected post-operation result.

For example, if a patient is young and active, the surgical planning system may pull up data about the treatment options for younger patients and suggest the user to consider partial knee arthroplasty (PKA) instead of total knee arthroplasty (TKA). The surgical planning system may further suggest the user to use guides along with a patient-specific implant while showing the best suited treatment options with minimum cartilage wear and tear.

The surgical planning system may also enable the user to view the treatment plan on a biomechanical model that includes bone and cartilage information along with soft tissue data, such as ligaments and muscle attachment. Further, the surgical planning system may also be configured to simulate the biomechanical model through rotations and translations and present data such as ligament elongations and knee loading so that minimum damage is caused to the soft tissue around the knee as a result of the treatment.

In some cases, the biomechanical model may be stored using one of the feedback loops described above and may be used as reference (along with navigation systems) during the surgery (in real-time) so that it may prompt the user (e.g., the surgeon) with warnings if the actual treatment deviates from the treatment plan or if other complications are encountered.

In some embodiments, intra-operative measurements, such as deviations from the pre-operative plans, soft tissue information, and the like may be stored to complete the patient profile and also to create future pre-operative plans and historical treatment data.

In some embodiments, intra-operative measurements, including deviations from the plan, may be recorded by the surgical planning system, such as: need for cementation (tibia/femur), patella, approach, alignment techniques, femoral rotation, femoral valgus, patella release, medial and lateral release, level of balance satisfaction achieved after the surgery (e.g., not happy, happy, very happy), blood loss, surgical time, range of motion at closure, use of robotic or other navigation systems, bone quality, diagnosis, PCL cut and size, limb alignment (varus/neutral/valgus), joint space opening before cuts (medial/lateral), joint space opening after implant placement (medial/lateral), laxity score (e.g., high/good/low), flexion contracture, ligament releases, patella resurfacing, use of tibia and/or femur guide and guide fit, tibial slope, proximal tibial cut, tibial implant, confirming if planned implant was used or other size and type, insert type and thickness of tibia, distal femur cut, posterior femur cut, AP-Shift femur, anterior femur cut, femur implant rotation, ROM: max flexion, balance in flexion, balance in extension, and others.

Further, post-operative data, such as PROM scores currently used by surgeons such as KSS, KOOS, OKS, EQ5D, FJS, etc., and other input provided by the patient or their therapists, during follow-ups may also be recorded by the surgical planning system.

In one example, medical images of the bone and/or cartilage anatomy of the patient, such as CT or MRI images, may be used to generate a three-dimensional model 2402 of the patient's knee. The defect can be quantified in the way described above.

Figure 24:
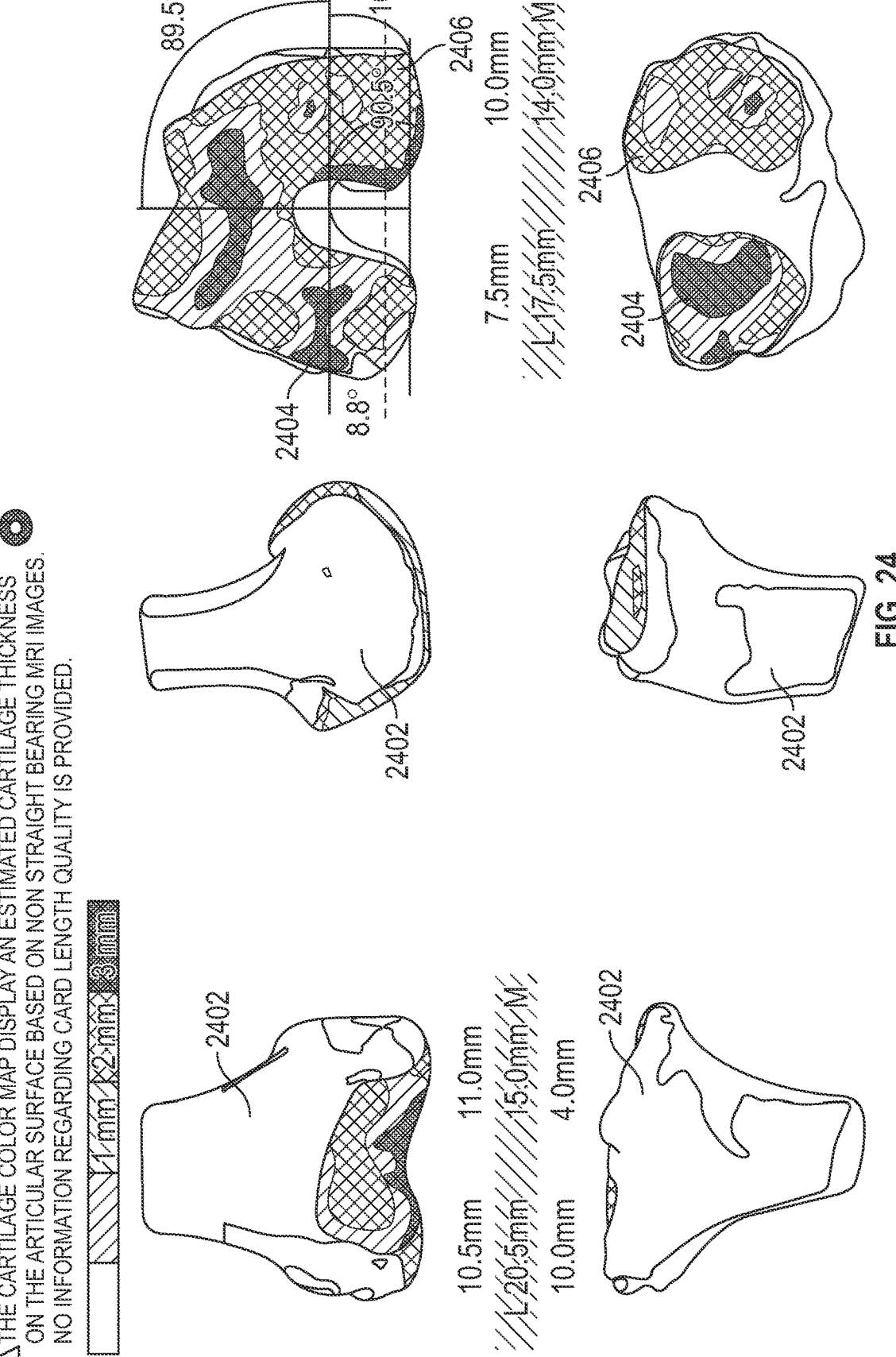
FIG. 24 depicts another example representation of a treatment option in a three-dimensional patient anatomy model.

For example, FIG. 24 depicts a representation of the cartilage thickness on the bony anatomy of a knee (tibia and femur). Certain identified areas (e.g., 2404) are considered to be healthy, such as where an adequate amount of cartilage is found. Other areas (e.g., 2406) indicate defects, such as weaker cartilage areas. This information may be used by a user (e.g., a surgeon) when deciding which treatment option to select for a treatment plan.

For example, a user may decide to treat the patient with a partial knee arthroplasty instead of total based on the images in FIG. 24, so that the cartilage found in the healthy areas may be saved. Based on this decision, the surgical planning system may suggest an implant, size, brand, and type for this patient from a variety of implants.

Further, the surgical planning system may be configured to allow a user to visualise the type and size of implant against cartilage wear before making a final decision for the treatment plan. In some embodiments, the user may further use historical data and patient population analysis to compare the type of implant, such as described above.

Figure 25:
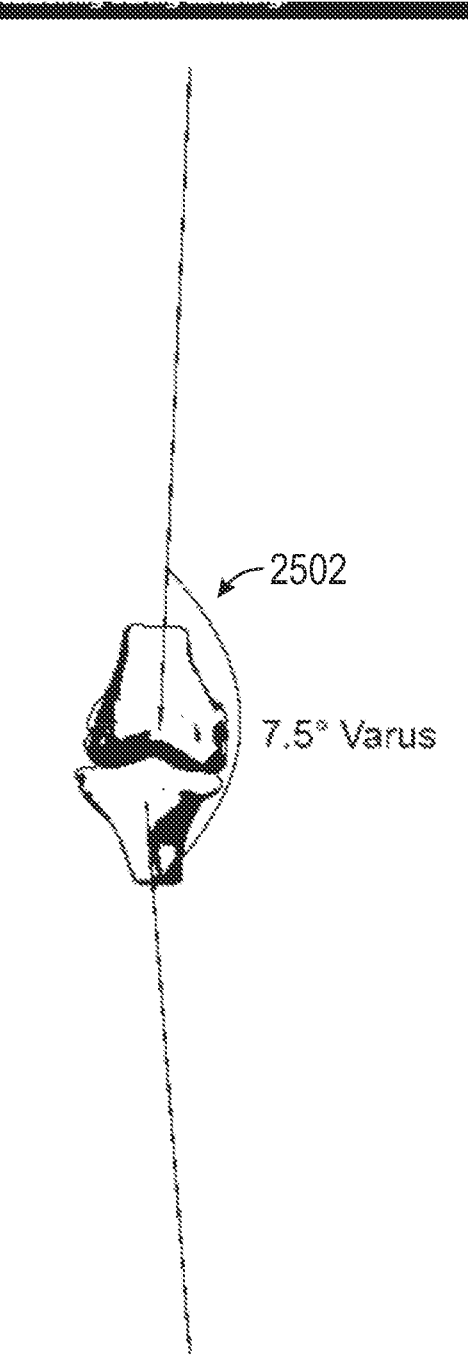
FIG. 25 depicts another example representation of a treatment option in a three-dimensional patient anatomy model.

Further, the surgical planning system may also be configured to display the varus/valgus angle 2502 used for limb alignment, such as depicted in FIG. 25.

Similarly, the surgical planning system may be configured to display other patient metrics, such as tibial slope, position, and location of implant, resection values, and others via a three-dimensional model.

Figure 26:
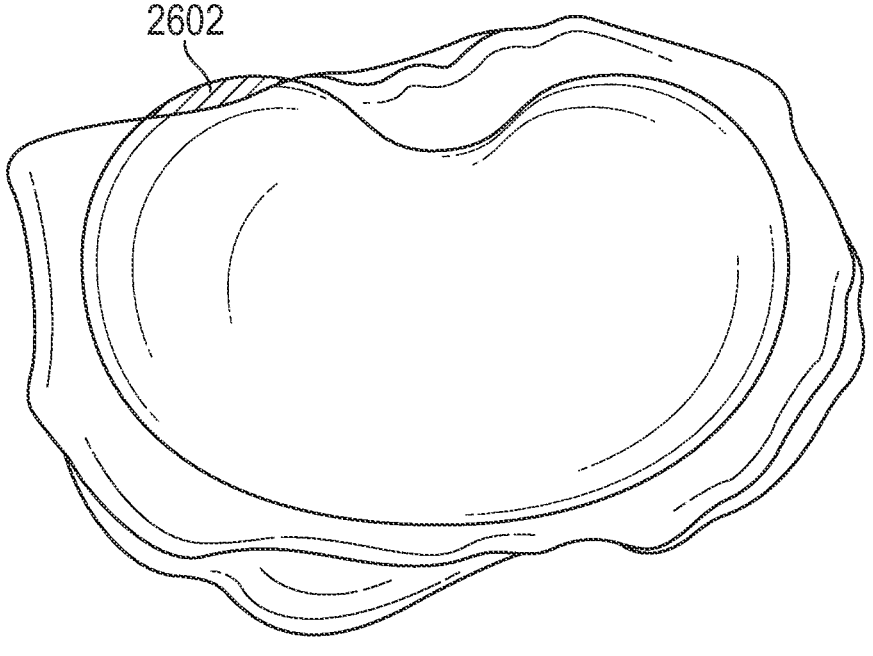
FIG. 26 depicts another example representation of a treatment option in a three-dimensional patient anatomy model.

Once, an implant is selected for a patient's anatomy, such as the implant shown in FIG. 26 for the patient's tibia, a user (e.g., surgeon) may further refine the position of the implant within the three-dimensional model. For example, if the implant overhangs (as depicted at 2602), the surgery planning system may warn the user and may suggest that the user revaluate the position of the implant. In some cases, if a suitable position is not established, the surgical planning system may suggest a different implant.

Example Methods

FIG. 27 depicts an example method 2700 for classifying a defect with a statistical shape model.

Method 2700 begins at step 2702 with acquiring medical image data associated with an anatomy of a patient.

Method 2700 then proceeds to step 2704 with creating a three-dimensional anatomy model based on the medical image data.

Method 2700 then proceeds to step 2706 with fitting a statistical shape model to the three-dimensional anatomy model.

Method 2700 then proceeds to step 2708 with determining one or more quantitative measurements based on the fitted statistical shape model.

Method 2700 then proceeds to step 2710 with classifying a defect associated with the anatomy of the patient based on the one or more quantitative measurements.

In some embodiments of method 2700, fitting the statistical shape model to the three-dimensional anatomy model further includes: subdividing the statistical shape model into a plurality of topological regions; and determining a subset of topological regions from the plurality of topological regions to use for fitting the statistical shape model to the three-dimensional anatomy model.

In some embodiments of method 2700, determining the subset of topological regions from the plurality of topological regions to use for fitting the statistical shape model to the three-dimensional anatomy model further includes: excluding a respective topological region of the plurality of topological regions if a fit error exceeds a threshold when the respective topological region is included in the subset of topological regions.

In some embodiments of method 2700, determining the subset of topological regions from the plurality of topological regions to use for fitting the statistical shape model to the three-dimensional anatomy model further comprises: selecting a first topological region from the plurality of topological regions; fitting the statistical shape model to the three-dimensional anatomy model based only on the first topological region; and calculating a first fit error based on a first fit of the statistical shape model based on the first topological region.

In some embodiments of method 2700, the first fit error is calculated as a root mean square error (RMSE) between a plurality of points on the statistical shape model and a plurality of corresponding points on the three-dimensional anatomy model.

In some embodiments of method 2700, determining the subset of topological regions from the plurality of topological regions to use for fitting the statistical shape model to the three-dimensional anatomy model further includes: determining that the first fit error is below a threshold; selecting a second topological region from the plurality of topological regions; fitting the statistical shape model to the three-dimensional anatomy model based on the second topological region; and calculating a second fit error based on a second fit of the statistical shape model based on the second topological region.

In some embodiments of method 2700, determining the subset of topological regions from the plurality of topological regions to use for fitting the statistical shape model to the three-dimensional anatomy model further includes: determining that the first fit error is above a threshold; and excluding a second topological region of the plurality of topological regions from the subset of topological regions based on the first fit error being above the threshold.

In some embodiments, method 2700 further includes: excluding a third topological region of the plurality of topological regions from the subset of topological regions based on excluding the second topological region.

In some embodiments of method 2700, the threshold is approximately 1.7 mm. In some embodiments of method 2700, the threshold is in a range of 0.5 mm to 3 mm.

In some embodiments of method 2700, determining the subset of topological regions from the plurality of topological regions to use for fitting the statistical shape model to the three-dimensional anatomy model further includes excluding a topological region of the plurality of topological regions known to be damaged or deformed from the subset of topological regions.

In some embodiments of method 2700, classifying the defect based on the one or more quantitative measurements further includes: combining two or more classification systems in order to generate a three-dimensional classification, wherein each of the two or more classification systems is based on a different perspective of the anatomy of the patient.

In some embodiments, method 2700 further includes creating a default treatment plan based on the classified defect associated with the anatomy of the patient.

In some embodiments, method 2700 further includes acquiring patient data associated with a plurality of patients having the classified defect; selecting a population of patient data based on a characteristic associated with the patient; and displaying a treatment option analysis comparing a plurality of treatment options based on the population of patient data.

In some embodiments, method 2700 further includes displaying a patient reference on the treatment option analysis based on the characteristic associated with the patient.

In some embodiments, method 2700 further includes modifying the default treatment plan based on the treatment option analysis.

In some embodiments of method 2700, the plurality of treatment options relate to treatment of a shoulder defect.

In some embodiments of method 2700, the plurality of treatment options relate to treatment of a joint defect.

In some embodiments of method 2700, the plurality of treatment options relate to treatment of a diseased part of the anatomy.

In some embodiments of method 2700, the plurality of treatment options relate to treatment of a defected part of the anatomy.

FIG. 28 depicts an example method 2800 for determining a treatment for an anatomical defect.

Method 2800 begins at step 2802 with acquiring medical image data associated with an anatomy of a patient.

Method 2800 then proceeds to step 2804 with creating a three-dimensional anatomy model based on the medical image data.

Method 2800 then proceeds to step 2806 with fitting a statistical shape model to the three-dimensional anatomy model.

Method 2800 then proceeds to step 2808 with identifying a defect based on the three-dimensional anatomy model and the statistical shape model.

Method 2800 then proceeds to step 2810 with determining a default treatment based on the identified defect.

Method 2800 then proceeds to step 2812 with receiving patient population data associated with a plurality of other patients having the identified defect, wherein the patient population data comprises a plurality of patient population data subsets associated with different treatments of the identified defect.

Method 2800 then proceeds to step 2814 with generating a visualization, comprising: a representation of each patient population data subset based on at least one patient characteristic; and a representation of the patient based on the at least one patient characteristic.

Method 2800 then proceeds to step 2816 with selecting a final treatment for the patient.

In some embodiments of method 2800, the final treatment comprises a modified default treatment.

In some embodiments of method 2800, the final treatment comprises the default treatment.

In some embodiments, method 2800 further includes generating a new patient population data entry based on a treatment outcome associated with the patient and the selected treatment.

In some embodiments of method 2800, fitting the statistical shape model to the three-dimensional anatomy model further includes: subdividing the statistical shape model into a plurality of topological regions; and determining a subset of topological regions from the plurality of topological regions to use for fitting the statistical shape model to the three-dimensional anatomy model.

In some embodiments of method 2800, determining the subset of topological regions from the plurality of topological regions to use for fitting the statistical shape model to the three-dimensional anatomy model further includes: excluding a respective topological region of the plurality of topological regions if a fit error exceeds a threshold when the respective topological region is included in the subset of topological regions.

In some embodiments of method 2800, determining the subset of topological regions from the plurality of topological regions to use for fitting the statistical shape model to the three-dimensional anatomy model further includes: selecting a first topological region from the plurality of topological regions; fitting the statistical shape model to the three-dimensional anatomy model based only on the first topological region; and calculating a first fit error based on a first fit of the statistical shape model based on the first topological region.

In some embodiments of method 2800, the first fit error is calculated as a root mean square error (RMSE) between a plurality of points on the statistical shape model and a plurality of corresponding points on the three-dimensional anatomy model.

In some embodiments of method 2800, determining the subset of topological regions from the plurality of topological regions to use for fitting the statistical shape model to the three-dimensional anatomy model further includes: determining that the first fit error is below a threshold; selecting a second topological region from the plurality of topological regions; fitting the statistical shape model to the three-dimensional anatomy model based on the second topological region; and calculating a second fit error based on a second fit of the statistical shape model based on the second topological region.

In some embodiments of method 2800, determining the subset of topological regions from the plurality of topological regions to use for fitting the statistical shape model to the three-dimensional anatomy model further includes: determining that the first fit error is above a threshold; and excluding a second topological region of the plurality of topological regions from the subset of topological regions based on the first fit error being above the threshold.

In some embodiments, method 2800 further includes excluding a third topological region of the plurality of topological regions from the subset of topological regions based on excluding the second topological region.

In some embodiments of method 2800, the threshold is approximately 1.7 mm.

In some embodiments of method 2800, the threshold is in a range of 0.5 mm to 3 mm.

In some embodiments of method 2800, determining the subset of topological regions from the plurality of topological regions to use for fitting the statistical shape model to the three-dimensional anatomy model further includes excluding a topological region of the plurality of topological regions known to be damaged or deformed from the subset of topological regions.

In some embodiments of method 2800, the final treatment relates to treatment of a shoulder defect.

In some embodiments of method 2800, the final treatment relates to treatment of a joint defect.

In some embodiments of method 2800, the final treatment relates to treatment of a diseased part of the anatomy.

In some embodiments of method 2800, the final treatment relates to treatment of a defected part of the anatomy.

FIG. 29 depicts an example method for determining a treatment for an anatomical defect.

Method 2900 begins at step 2902 with acquiring medical image data associated with an anatomy of a patient.

Method 2900 then proceeds to step 2904 with creating a three-dimensional anatomy model based on the medical image data.

Method 2900 then proceeds to step 2906 with fitting a statistical shape model to the three-dimensional anatomy model.

Method 2900 then proceeds to step 2908 with identifying a defect based on the three-dimensional anatomy model and the statistical shape model.

Method 2900 then proceeds to step 2910 with receiving a default treatment plan using the historical data analysis, wherein the historical data comprises previously used preoperative treatment plans for the identified defect.

Method 2900 then proceeds to step 2912, optionally, with generating a visualization, comprising: a representation of treatment plan based on at least one patient characteristic; and a representation of the patient based on the at least one patient characteristic.

Method 2900 then proceeds to step 2914 with approval of a final treatment for the patient.

In some embodiments of method 2900, the final treatment comprises a modified default treatment.

In some embodiments of method 2900, the final treatment comprises the default treatment.

In some embodiments, method 2900 further includes generating a new patient population data entry based on a treatment outcome associated with the patient and the selected treatment.

In some embodiments of method 2900, fitting the statistical shape model to the three-dimensional anatomy model further includes: subdividing the statistical shape model into a plurality of topological regions; and determining a subset of topological regions from the plurality of topological regions to use for fitting the statistical shape model to the three-dimensional anatomy model.

In some embodiments of method 2900, determining the subset of topological regions from the plurality of topological regions to use for fitting the statistical shape model to the three-dimensional anatomy model further includes: excluding a respective topological region of the plurality of topological regions if a fit error exceeds a threshold when the respective topological region is included in the subset of topological regions.

In some embodiments of method 2900, determining the subset of topological regions from the plurality of topological regions to use for fitting the statistical shape model to the three-dimensional anatomy model further includes: selecting a first topological region from the plurality of topological regions; fitting the statistical shape model to the three-dimensional anatomy model based only on the first topological region; and calculating a first fit error based on a first fit of the statistical shape model based on the first topological region.

In some embodiments of method 2900, the first fit error is calculated as a root mean square error (RMSE) between a plurality of points on the statistical shape model and a plurality of corresponding points on the three-dimensional anatomy model.

In some embodiments of method 2900, determining the subset of topological regions from the plurality of topological regions to use for fitting the statistical shape model to the three-dimensional anatomy model further includes: determining that the first fit error is below a threshold; selecting a second topological region from the plurality of topological regions; fitting the statistical shape model to the three-dimensional anatomy model based on the second topological region; and calculating a second fit error based on a second fit of the statistical shape model based on the second topological region.

In some embodiments of method 2900, determining the subset of topological regions from the plurality of topological regions to use for fitting the statistical shape model to the three-dimensional anatomy model further includes: determining that the first fit error is above a threshold; and excluding a second topological region of the plurality of topological regions from the subset of topological regions based on the first fit error being above the threshold.

In some embodiments, method 2900 further includes excluding a third topological region of the plurality of topological regions from the subset of topological regions based on excluding the second topological region.

In some embodiments of method 2900, the threshold is approximately 1.7 mm.

In some embodiments of method 2900, the threshold is in a range of 0.5 mm to 3 mm.

In some embodiments of method 2900, determining the subset of topological regions from the plurality of topological regions to use for fitting the statistical shape model to the three-dimensional anatomy model further includes excluding a topological region of the plurality of topological regions known to be damaged or deformed from the subset of topological regions.

In some embodiments of method 2900, the final treatment relates to treatment of a shoulder defect.

In some embodiments of method 2900, the final treatment relates to treatment of a joint defect.

In some embodiments of method 2900, the final treatment relates to treatment of a diseased part of the anatomy.

In some embodiments of method 2900, the final treatment relates to treatment of a defected part of the anatomy.

Example Processing System

Figure 30:
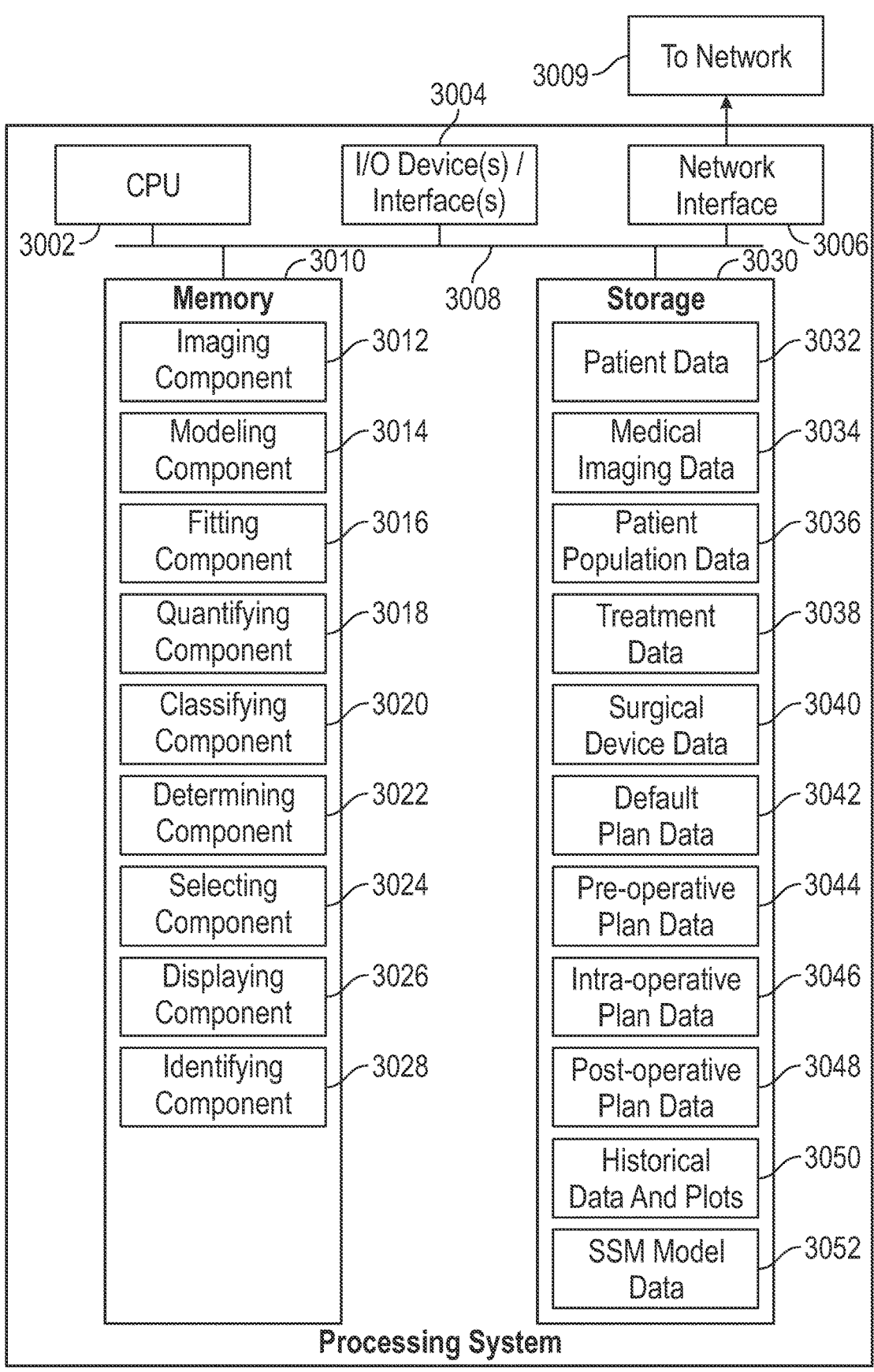
FIG. 30 depicts an example processing system that may be configured to perform the various methods described herein.

FIG. 30 depicts an exemplary processing system 3000 configured to perform methods for detecting and removing personally identifiable information.

Processing system 3000 includes a CPU 3002 connected to a data bus 3008. CPU 3002 is configured to process computer-executable instructions, e.g., stored in memory 3010 or storage 3030, and to cause processing system 3000 to perform methods as described herein, for example with respect to FIGS. 27-29. CPU 3002 is included to be representative of a single CPU, multiple CPUs, a single CPU having multiple processing cores, and other forms of processing architecture capable of executing computer-executable instructions.

Processing system 3000 further includes input/output devices and interface 3004, which allows processing system 3000 to interface with input/output devices, such as, for example, keyboards, displays, mouse devices, pen input, touch sensitive input devices, cameras, microphones, medical imaging equipment, and other devices that allow for interaction with processing system 3000. Note that while not depicted with independent external I/O devices, processing system 3000 may connect with external I/O devices through physical and wireless connections (e.g., an external display device).

Processing system 3000 further includes network interface 3006, which provides processing system 3000 with access to external computing devices, such as via network 3009.

Processing system 3000 further includes memory 3010, which in this example includes various components configured to perform the functions described herein. In this embodiments, memory 3010 includes imaging component 3012, modeling component 3014, fitting component 3016, quantifying component 3018, classifying component 3020, determining component 3022, selecting component 3024, displaying 3026, and identifying component 3028. These various components may, for example, comprise computer-executable instructions configured to perform the various functions described herein.

Note that while shown as a single memory 3010 in FIG. 30 for simplicity, the various aspects stored in memory 3010 may be stored in different physical memories, but all accessible CPU 3002 via internal data connections, such as bus 3012. For example, some components of memory 3010 may be locally resident on processing system 3000, while others may be performed on remote processing systems or in cloud-based processing systems in other embodiments. This is just one example.

Processing system 3000 further includes storage 3030, which in this example includes patient data 3032, medical imaging data 3034, patient population data 3036, treatment data 3038, surgical device data 3040, default plan data 3042, pre-operating plan data 3044, intra-operative plan data 3046, post-operative plan data 3048, historical data and plot 3050, and SSM model data 3052. While not depicted in FIG. 30, other aspects may be included in storage 3030.

As with memory 3010, a single storage 3030 is depicted in FIG. 30 for simplicity, but the various aspects stored in storage 3030 may be stored in different physical storages, but all accessible to CPU 3002 via internal data connections, such as bus 3008, or external connection, such as network interface 3006.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and other circuit elements that are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:

acquiring medical image data associated with an anatomy of a patient;

creating a three-dimensional anatomy model based on the medical image data;

fitting a statistical shape model of a statistical healthy anatomy to the three-dimensional anatomy model, wherein the fitted statistical shape model comprises a virtual model of a predicted healthy version of the anatomy of the patient, wherein fitting the statistical shape model to the three-dimensional anatomy model comprises:

subdividing the statistical shape model into a plurality of topological regions; and determining a subset of topological regions from the plurality of topological regions to use for fitting the statistical shape model to the three-dimensional anatomy model, wherein determining the subset of topological regions from the plurality of topological regions to use for fitting the statistical shape model to the three-dimensional anatomy model further comprises: excluding at least one topological region of the plurality of topological regions based on a fit error exceeding a threshold based on the at least one topological region being included in the subset of topological regions;

determining one or more quantitative measurements based on the fitted statistical shape model;

classifying a defect associated with the anatomy of the patient based on the one or more quantitative measurements; and displaying 1) the virtual model superimposed with the three-dimensional anatomy model; and 2) an indication of the classified defect.

2. The method of claim 1, wherein determining the subset of topological regions from the plurality of topological regions to use for fitting the statistical shape model to the three-dimensional anatomy model further comprises:

selecting a first topological region from the plurality of topological regions;

fitting the statistical shape model to the three-dimensional anatomy model based only on the first topological region; and calculating a first fit error based on a first fit of the statistical shape model based on the first topological region.

3. The method of claim 2, wherein the first fit error is calculated as a root mean square error (RMSE) between a plurality of points on the statistical shape model and a plurality of corresponding points on the three-dimensional anatomy model.

4. The method of claim 2, wherein determining the subset of topological regions from the plurality of topological regions to use for fitting the statistical shape model to the three-dimensional anatomy model further comprises:

determining that the first fit error is below the threshold;

selecting a second topological region from the plurality of topological regions;

fitting the statistical shape model to the three-dimensional anatomy model based on the second topological region; and calculating a second fit error based on a second fit of the statistical shape model based on the second topological region.

5. The method of claim 2, wherein determining the subset of topological regions from the plurality of topological regions to use for fitting the statistical shape model to the three-dimensional anatomy model further comprises:

determining that the first fit error is above the threshold; and excluding a second topological region of the plurality of topological regions from the subset of topological regions based on the first fit error being above the threshold.

6. The method of claim 5, further comprising: excluding a third topological region of the plurality of topological regions from the subset of topological regions based on excluding the second topological region.

7. The method of claim 1, wherein the threshold is approximately 1.7 mm.

8. The method of claim 1, wherein the threshold is in a range of 0.5 mm to 3 mm.

9. The method of claim 1, wherein determining the subset of topological regions from the plurality of topological regions to use for fitting the statistical shape model to the three-dimensional anatomy model further comprises: excluding a topological region of the plurality of topological regions known to be damaged or deformed from the subset of topological regions.

10. The method of claim 1, wherein classifying the defect based on the one or more quantitative measurements further comprises:

combining two or more classification systems in order to generate a three-dimensional classification, wherein each of the two or more classification systems is based on a different perspective of the anatomy of the patient.

11. The method of claim 1, further comprising: creating a default treatment plan based on the classified defect associated with the anatomy of the patient.

12. The method of claim 11, further comprising:

acquiring patient data associated with a plurality of patients having the classified defect;

selecting a population of patient data based on a characteristic associated with the patient; and displaying a treatment option analysis comparing a plurality of treatment options based on the population of patient data.

13. The method of claim 12, further comprising: displaying a patient reference on the treatment option analysis based on the characteristic associated with the patient.

14. The method of claim 13, further comprising: modifying the default treatment plan based on the treatment option analysis.

15. The method of claim 12, wherein the plurality of treatment options relate to treatment of a shoulder defect.

16. The method of claim 12, wherein the plurality of treatment options relate to treatment of a joint defect.

17. The method of claim 12, wherein the plurality of treatment options relate to treatment of a diseased part of the anatomy.

18. The method of claim 12, wherein the plurality of treatment options relate to treatment of a defected part of the anatomy.

19. A system, comprising:

at least one memory; and at least one processor, the at least one processor configured to:

acquire medical image data associated with an anatomy of a patient;

create a three-dimensional anatomy model based on the medical image data;

fit a statistical shape model of a statistical healthy anatomy to the three-dimensional anatomy model, wherein the fitted statistical shape model comprises a virtual model of a predicted healthy version of the anatomy of the patient, wherein to fit the statistical shape model to the three-dimensional anatomy model comprises to:

subdivide the statistical shape model into a plurality of topological regions; and determine a subset of topological regions from the plurality of topological regions to use for fitting the statistical shape model to the three-dimensional anatomy model, wherein to determine the subset of topological regions from the plurality of topological regions to use to fit the statistical shape model to the three-dimensional anatomy model further comprises: to exclude at least one topological region of the plurality of topological regions based on a fit error exceeding a threshold based on the at least one topological region being included in the subset of topological regions;

determine one or more quantitative measurements based on the fitted statistical shape model;

classify a defect associated with the anatomy of the patient based on the one or more quantitative measurements; and display 1) the virtual model superimposed with the three-dimensional anatomy model; and 2) an indication of the classified defect.

20. A non-transitory computer readable medium comprising instructions, that when executed by a system, cause the system to:

acquire medical image data associated with an anatomy of a patient;

create a three-dimensional anatomy model based on the medical image data;

fit a statistical shape model of a statistical healthy anatomy to the three-dimensional anatomy model, wherein the fitted statistical shape model comprises a virtual model of a predicted healthy version of the anatomy of the patient, wherein to fit the statistical shape model to the three-dimensional anatomy model comprises to:

subdivide the statistical shape model into a plurality of topological regions; and determine a subset of topological regions from the plurality of topological regions to use for fitting the statistical shape model to the three-dimensional anatomy model, wherein to determine the subset of topological regions from the plurality of topological regions to use to fit the statistical shape model to the three-dimensional anatomy model further comprises: to exclude at least one topological region of the plurality of topological regions based on a fit error exceeding a threshold based on the at least one topological region being included in the subset of topological regions;

determine one or more quantitative measurements based on the fitted statistical shape model;

classify a defect associated with the anatomy of the patient based on the one or more quantitative measurements; and display 1) the virtual model superimposed with the three-dimensional anatomy model; and 2) an indication of the classified defect.

* * * * *